(12) United States Patent
Line et al.

(10) Patent No.: US 11,292,376 B2
(45) Date of Patent: Apr. 5, 2022

(54) SEATING ASSEMBLY FOR A VEHICLE WITH SOURCE OF LIQUID SANITIZER AND NOZZLES TO DISPENSE LIQUID SANITIZER ONTO EXTERIOR SURFACE OF SEATING ASSEMBLY TO SANITIZE THE EXTERIOR SURFACE

(71) Applicant: Ford Global Technologies, LLC, Dearborn, MI (US)

(72) Inventors: Johnathan Andrew Line, Northville, MI (US); Michael Kolich, Windsor (CA); Daniel Ferretti, Commerce Township, MI (US); Scott Holmes Dunham, Redford, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 17/060,514

(22) Filed: Oct. 1, 2020

(65) Prior Publication Data

US 2021/0016698 A1     Jan. 21, 2021

Related U.S. Application Data

(62) Division of application No. 16/286,788, filed on Feb. 27, 2019, now Pat. No. 10,836,291.

(51) Int. Cl.
*B60N 2/60*     (2006.01)
*B60N 2/90*     (2018.01)
(Continued)

(52) U.S. Cl.
CPC .............. *B60N 2/90* (2018.02); *B08B 3/08* (2013.01); *B60N 2/242* (2013.01); *A61L 2/18* (2013.01);
(Continued)

(58) Field of Classification Search
CPC ........ B60N 2/90; B60N 2/986; B60N 2/2872; B60N 2/885; B60N 2/99; B64D 11/0606; B64D 11/064; B08B 3/08
See application file for complete search history.

(56) References Cited

U.S. PATENT DOCUMENTS 5,795,018 A * 8/1998 Schumacher ...... B64D 11/0632
297/184.17
5,857,745 A * 1/1999 Matsumiya ............ B60N 2/995
297/354.13
(Continued)

FOREIGN PATENT DOCUMENTS

DE     102016215247 A1     2/2018
DE     102018002328 A1     9/2019
(Continued)

OTHER PUBLICATIONS

US 10,276,605 B2, 08/2019, Majdali et al. (withdrawn)

*Primary Examiner* — Syed A Islam
(74) *Attorney, Agent, or Firm* — Vichit Chea; Price Heneveld LLP

(57) ABSTRACT

A vehicle comprises: a plurality of seating assemblies, each seating assembly including an exterior surface, an interior beneath the exterior surface, a pressured supply of liquid sanitizer disposed within the interior, and at least one valve in fluid communication with the pressurized supply of liquid sanitizer that opens to allow liquid sanitizer to be dispensed onto the exterior surface. Each of the at least one valve are selectively positionable to and from an open position where the liquid sanitizer flows through the valve to allow liquid sanitizer to be dispensed onto the exterior surface and a closed position where the liquid sanitizer cannot flow through the valve. A controller, configured to receive instructions from a user interface, communicates with each
(Continued)

of the at least one valve to cause any particular valve to move to and from the open position and the closed position.

20 Claims, 16 Drawing Sheets

(51) Int. Cl.
  *B08B 3/08*     (2006.01)
  *B60N 2/24*     (2006.01)
  *A61L 2/18*     (2006.01)
  *B60N 2/56*     (2006.01)
  *B60N 2/28*     (2006.01)
  *B64D 11/06*    (2006.01)

(52) U.S. Cl.
  CPC .......... *B60N 2/2872* (2013.01); *B60N 2/5614* (2013.01); *B60N 2/986* (2018.02); *B64D 11/0604* (2014.12); *B64D 11/0606* (2014.12)

(56) References Cited

U.S. PATENT DOCUMENTS

| | | | |
|---|---|---|---|
| 6,046,754 A * | 4/2000 | Stanek | G06F 1/1603 |
| | | | 345/169 |
| 6,644,736 B2 * | 11/2003 | Nguyen | B64D 11/0606 |
| | | | 297/184.17 |
| 7,568,759 B2 * | 8/2009 | Schurg | B64D 11/0644 |
| | | | 297/184.1 |
| 9,592,312 B2 | 3/2017 | Lyslo et al. | |
| 9,956,898 B1 * | 5/2018 | Dellock | B60K 37/04 |
| 9,993,124 B2 | 6/2018 | Poleki | |
| 10,059,238 B1 * | 8/2018 | Salter | B60N 2/90 |
| 2006/0001302 A1 * | 1/2006 | Achilles | B64D 11/0606 |
| | | | 297/284.1 |
| 2006/0043777 A1 * | 3/2006 | Friedman | B60N 2/99 |
| | | | 297/216.13 |
| 2006/0097553 A1 * | 5/2006 | Spurlock | B64D 11/0604 |
| | | | 297/248 |
| 2007/0053188 A1 | 3/2007 | New et al. | |
| 2007/0207066 A1 | 9/2007 | Thur et al. | |
| 2008/0175761 A1 | 7/2008 | Thur et al. | |
| 2014/0096314 A1 | 4/2014 | Ferro | |
| 2016/0000951 A1 | 1/2016 | Kreiner et al. | |
| 2016/0073787 A1 * | 3/2016 | Jamele | A63G 31/16 |
| | | | 297/217.1 |
| 2016/0089459 A1 | 3/2016 | Boodaghians et al. | |
| 2016/0250362 A1 | 9/2016 | Mackin | |
| 2018/0064833 A1 | 3/2018 | Childress et al. | |
| 2018/0235416 A1 * | 8/2018 | Poleki | A47K 13/302 |
| 2018/0361002 A1 | 12/2018 | Mastrocola | |
| 2021/0009272 A1 * | 1/2021 | Klaus | B64D 11/0626 |

FOREIGN PATENT DOCUMENTS

| | | |
|---|---|---|
| EP | 2668964 A1 | 12/2013 |
| JP | 2005130994 A | 5/2005 |

* cited by examiner

SEATING ASSEMBLY FOR A VEHICLE WITH SOURCE OF LIQUID SANITIZER AND NOZZLES TO DISPENSE LIQUID SANITIZER ONTO EXTERIOR SURFACE OF SEATING ASSEMBLY TO SANITIZE THE EXTERIOR SURFACE

CROSS-REFERENCE TO RELATED APPLICATIONS

This application is a divisional application that claims priority to and the benefit under 35 U.S.C. § 121 of U.S. patent application Ser. No. 16/286,788, which was filed on Feb. 27, 2019, entitled "SEATING ASSEMBLY FOR A VEHICLE WITH SOURCE OF LIQUID SANITIZER AND NOZZLES TO DISPENSE LIQUID SANITIZER ONTO EXTERIOR SURFACE OF SEATING ASSEMBLY TO SANITIZE THE EXTERIOR SURFACE," (now U.S. Pat. No. 10,836,291) the entire disclosure of which is hereby incorporated by reference herein.

FIELD OF THE INVENTION

The present invention generally relates to a seating assembly for a vehicle, and more particularly, to a seating assembly for a vehicle having a source of liquid sanitizer to allow for the self-sanitization of an exterior surface of the seating assembly.

BACKGROUND OF THE INVENTION

A person, as an anticipated passenger of a seating assembly of a vehicle that is routinely occupied by other passengers, feels uneasy about the level of sanitization of the seating assembly that the person will soon occupy. Previous other passengers of the seating assembly might have been sick, or might have been transporting malodorous animals.

SUMMARY OF THE INVENTION

According to a first aspect of the present invention, a seating assembly for a vehicle comprises: an exterior surface; an interior beneath the exterior surface; a pressurized supply of liquid sanitizer disposed within the interior; a nozzle in fluid communication with the pressurized supply of liquid sanitizer; a valve in fluid communication between the pressurized supply of liquid sanitizer and the at least one nozzle, the valve selectively positionable to and from an open position where the liquid sanitizer flows through the valve to the nozzle and a closed position where the liquid sanitizer cannot flow through the valve; and the nozzle directing liquid sanitizer onto the exterior surface when the valve is in the open position.

Embodiments of the first aspect of the invention can include any one or a combination of the following features:
  a controller in communication with the valve to cause the valve to move to and from the open position and the closed position, the controller configured to receive instructions from a user interface regarding whether the controller is to cause the valve to move to the open position;
  the user interface is a touch screen display on a mobile communications device, and the controller is in communication with the mobile communications device;
  a plurality of nozzles in addition to the nozzle, each of the plurality of nozzles in fluid communication with the pressurized supply of liquid sanitizer;
  a plurality of valves in addition to the valve, each of the plurality of valves are in fluid communication with one or more of the plurality of nozzles and in fluid communication with the pressurized supply of liquid sanitizer through a manifold in fluid communication with the pressurized supply of liquid sanitizer, each of the plurality of valves are selectively positionable to, from, and between an open position where the liquid sanitizer flows through the valve to one or more of the plurality of nozzles, and a closed position where the liquid sanitizer cannot flow through the valve to any of the plurality of nozzles;
  each of the plurality of nozzles directs liquid sanitizer onto the exterior surface when the valve in fluid communication with the nozzle is in the open position;
  each of the plurality of nozzles are positioned to direct liquid sanitizer onto different a target area of the exterior surface, each target area overlapping at least one other target area;
  a seatback, a seat, and at least one of the plurality of nozzles is positioned at the seatback, and at least one of the plurality of nozzles is positioned at the seat;
  at least one armrest, and at least one of the plurality of nozzles is positioned at the at least one armrest;
  the nozzle compresses a portion of the exterior surface toward the interior;
  the seating assembly further comprises a seatbelt, and the at least one of the plurality of nozzles is positioned to direct liquid sanitizer onto the seatbelt;
  the nozzle comprises an inlet for the liquid sanitizer and perforations in fluid communication with the inlet through which the liquid sanitizer flows to direct liquid sanitizer onto the exterior surface when the valve is in the open position, the inlet being disposed within the interior and the perforations exposed at the exterior surface;
  a carrier providing structural support within the interior, the carrier including an inlet, an outlet, and a fluid communication pathway between the inlet and the outlet, through which liquid sanitizer flows from the valve toward the nozzle when the valve is in the open position;
  cushioning disposed in the interior between the exterior surface, and a flexible conduit extending from the carrier through the cushioning;
  the nozzle comprises an inlet for the liquid sanitizer and perforations in fluid communication with the inlet, the perforations being exposed at the exterior surface;
  the flexible conduit has a first end attached to inlet of the nozzle within the interior and a second end fluidly coupled to the outlet of the carrier; and
  when the valve is in the open position, liquid sanitizer flows through the valve, through the fluid communication pathway of the carrier system, through the flexible conduit, and then out of the perforations of the nozzle and onto the exterior surface.

According to a second aspect of the present invention, a seating assembly for a vehicle comprises: an exterior surface; an interior beneath the exterior surface; a seat; a seatback cooperating with the seat, the seatback having lateral sides, a bottom portion, and a top portion; a pressurized supply of liquid sanitizer disposed within the interior; and a dispenser disposed at one of the lateral sides of the seatback. The dispenser includes a fixed base that extends along the lateral side from between the bottom portion of the seatback and the top portion of the seatback; a forward arm pivotally attached to the fixed base closer to the bottom portion of the seatback than the top portion of the seatback; a first flexible sheet of material attached at one end to the fixed base and at another end to the forward arm, the first flexible sheet of material having perforations in fluid communication with the pressurized supply of liquid sanitizer; a stowed position where the forward arm is adjacent to the fixed base with the first flexible sheet of material folded together and the dispenser not dispensing liquid sanitizer through the perforations onto the exterior surface; and a deployed position where the forward arm is rotated forward away from the fixed base with the first flexible sheet of material fanned out and the dispenser dispenses liquid sanitizer through the perforations onto the exterior surface.

Embodiments of the second aspect of the invention can include any one or a combination of the following features:
- a second flexible sheet of material layered next to the first flexible sheet of material, with the second flexible sheet of material being positioned laterally further away from a midline of the seating assembly than the first flexible sheet of material, the second flexible sheet of material and the first flexible sheet of material cooperating to form a fluid flow zone between the second flexible sheet of material and the first flexible sheet of material, with the first flexible sheet of material and the second flexible sheet of material having an interior surface facing the fluid flow zone;
- in the stowed position, the second flexible sheet of material and the first flexible sheet of material are folded together;
- in the deployed position, the second flexible sheet of material is also fanned out, and liquid sanitizer flows within the fluid flow zone between the first flexible sheet of material and the second flexible sheet of material before exiting through the perforations of the first flexible sheet of material;
- a plurality of dividers, each attached to the interior surface of the first flexible sheet of material and the interior surface of the second flexible sheet of material, maintaining separation between the first flexible sheet of material and the second flexible sheet of material, and including channels in fluid communication with the fluid flow zone to allow for the flow of liquid sanitizer through the plurality of dividers;
- a valve in fluid communication with and between the pressurized supply of liquid sanitizer and the first dispenser, the valve selectively positionable to and from an open position where the liquid sanitizer flows through the valve to the first dispenser and a closed position where the liquid sanitizer cannot flow through the valve to the dispenser;
- a controller in communication with the valve to cause the valve to move to and from the open position and the closed position, the controller configured to receive instructions from a user interface regarding whether the controller is to cause the valve to move to the open position;
- a second dispenser disposed at the other of the lateral sides of the seatback, the second dispenser including: a fixed base that extends along the lateral side from between the bottom portion of the seatback and the top portion of the seatback; a forward arm pivotally attached to the fixed base closer to the bottom portion of the seatback than the top portion of the seatback; a first flexible sheet of material attached at one side to the fixed base and at another side to the forward arm, the first flexible sheet of material having perforations in fluid communication with the pressurized supply of liquid sanitizer; a stowed position where the forward arm is adjacent to the fixed base with the first flexible sheet of material folded together and the dispenser not dispensing liquid sanitizer through the perforations onto the exterior surface; and a deployed position where the forward arm is rotated forward away from the fixed base with the first flexible sheet of material fanned out and the dispenser dispenses liquid sanitizer through the perforations onto the exterior surface; and
- when the dispenser is in the deployed position and the second dispenser is in the deployed position, the dispenser faces the second dispenser, and the dispenser and the second dispenser dispense liquid sanitizer onto the exterior surface from generally opposite directions.

According to a third aspect of the present invention, a vehicle comprises: a plurality of seating assemblies, each seating assembly including an exterior surface, an interior beneath the exterior surface, a pressured supply of liquid sanitizer disposed within the interior, and at least one valve in fluid communication with the pressurized supply of liquid sanitizer that opens to allow liquid sanitizer to be dispensed onto the exterior surface.

Embodiments of the third aspect of the invention can include any one or a combination of the following features:
- each of the at least one valve are selectively positionable to and from an open position where the liquid sanitizer flows through the valve to allow liquid sanitizer to be dispensed onto the exterior surface and a closed position where the liquid sanitizer cannot flow through the valve;
- a controller in communication with each of the at least one valve to cause any particular valve to move to and from the open position and the closed position, the controller configured to receive instructions from a user interface regarding whether the controller is to cause the valve to move to the open position;
- the vehicle is an intercity passenger service vehicle;
- the user interface is disposed exterior of the vehicle, with the instructions transmitted to the controller;
- the instructions were issued by an anticipated passenger of the vehicle, and the controller caused the valve to move to the open position before the anticipated passenger boarded the vehicle; and
- each seating assembly further includes a plurality of nozzles and a plurality of valves, each of the plurality of valves being in fluid communication with one of the plurality of nozzles and in fluid communication with the pressurized supply of liquid sanitizer through a manifold in fluid communication with the pressurized supply of liquid sanitizer, each of the plurality of valves selectively positionable to and from an open position where the liquid sanitizer flows through the valve to one of the plurality of nozzles, and a closed position where the liquid sanitizer cannot flow through the valve to one of the plurality of nozzles.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 2:
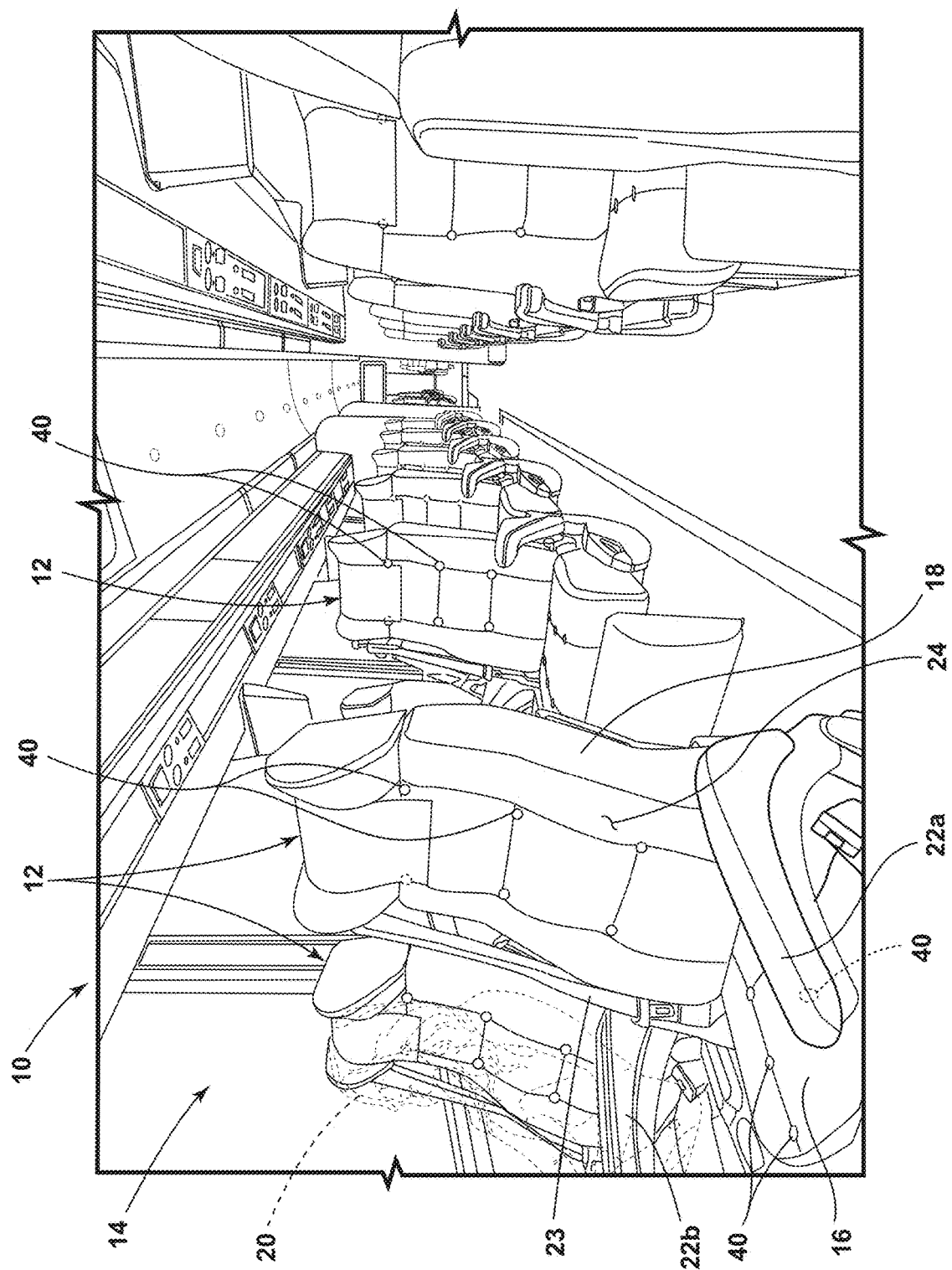
FIG. 2 is a perspective view of the interior of the vehicle of FIG. 1, illustrating a plurality of seating assemblies, each having an exterior surface and nozzles exposed over the exterior surface.

For purposes of description herein, the terms "beneath," "forward," "top," and "bottom," and derivatives thereof, shall relate to the invention as oriented in FIG. 2. However, it is to be understood that the invention may assume various alternative orientations, except where expressly specified to the contrary. It is also to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
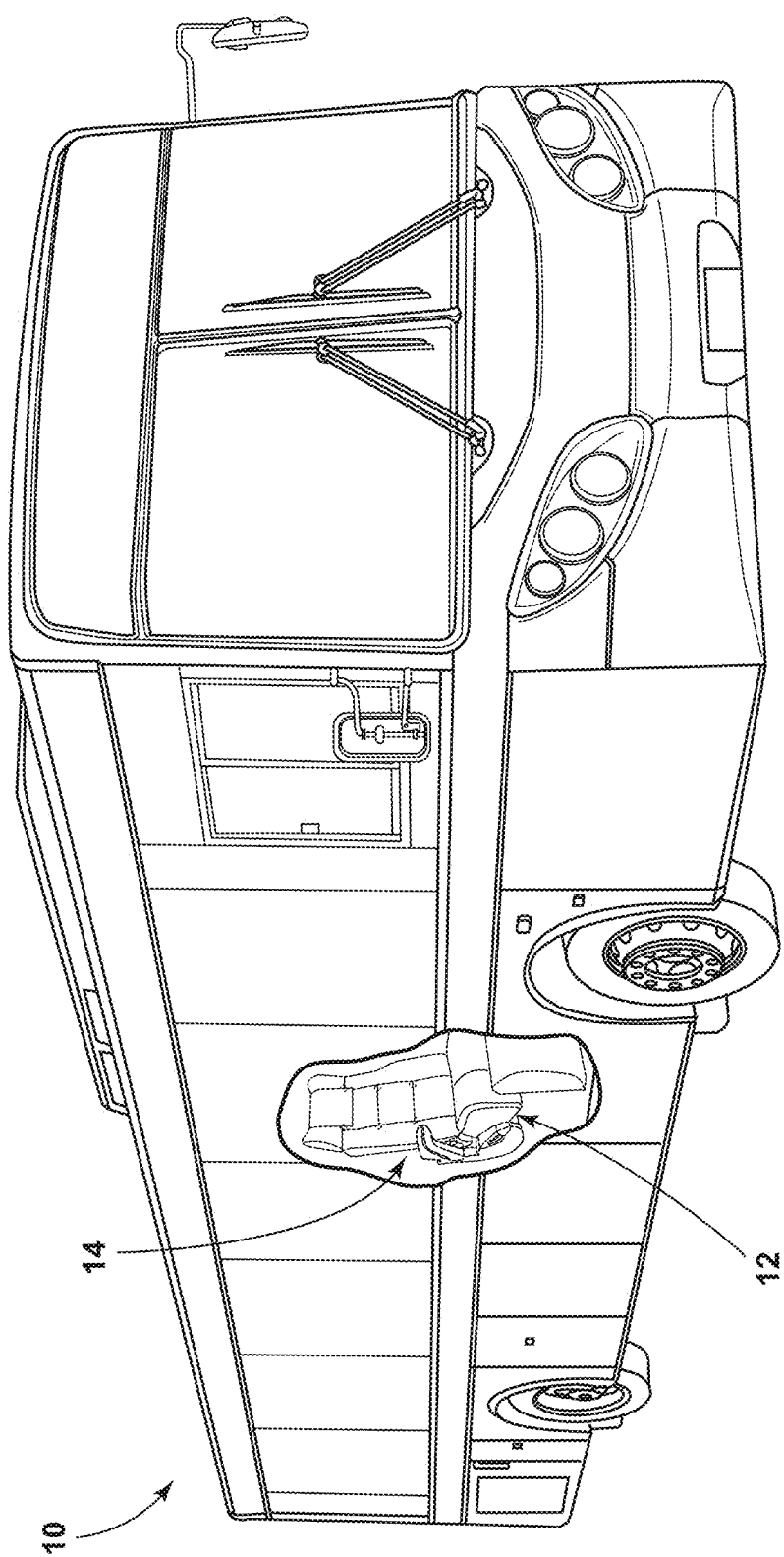
FIG. 1 is a perspective view of a vehicle, specifically a passenger transport bus, illustrating a cut-away view into an interior where there is a seating assembly.

Referring to FIGS. 1-2, a vehicle 10 includes a plurality of seating assemblies 12 disposed throughout an interior 14. Each of the plurality of seating assemblies 12 include a seat 16 and a seatback 18, both cooperating to support a person 20 sitting in the seating assembly 12. In the illustrated embodiment, each seating assembly 12 additionally includes a pair of armrests 22 and a seatbelt 23. The vehicle 10 can be a vehicle 10 used in public transport, as a vehicle-for-hire, or as an intercity passenger service vehicle 10. The vehicle 10 can be a bus, an airplane, a railcar, a car, a truck, or a van, among other things.

Figure 3:
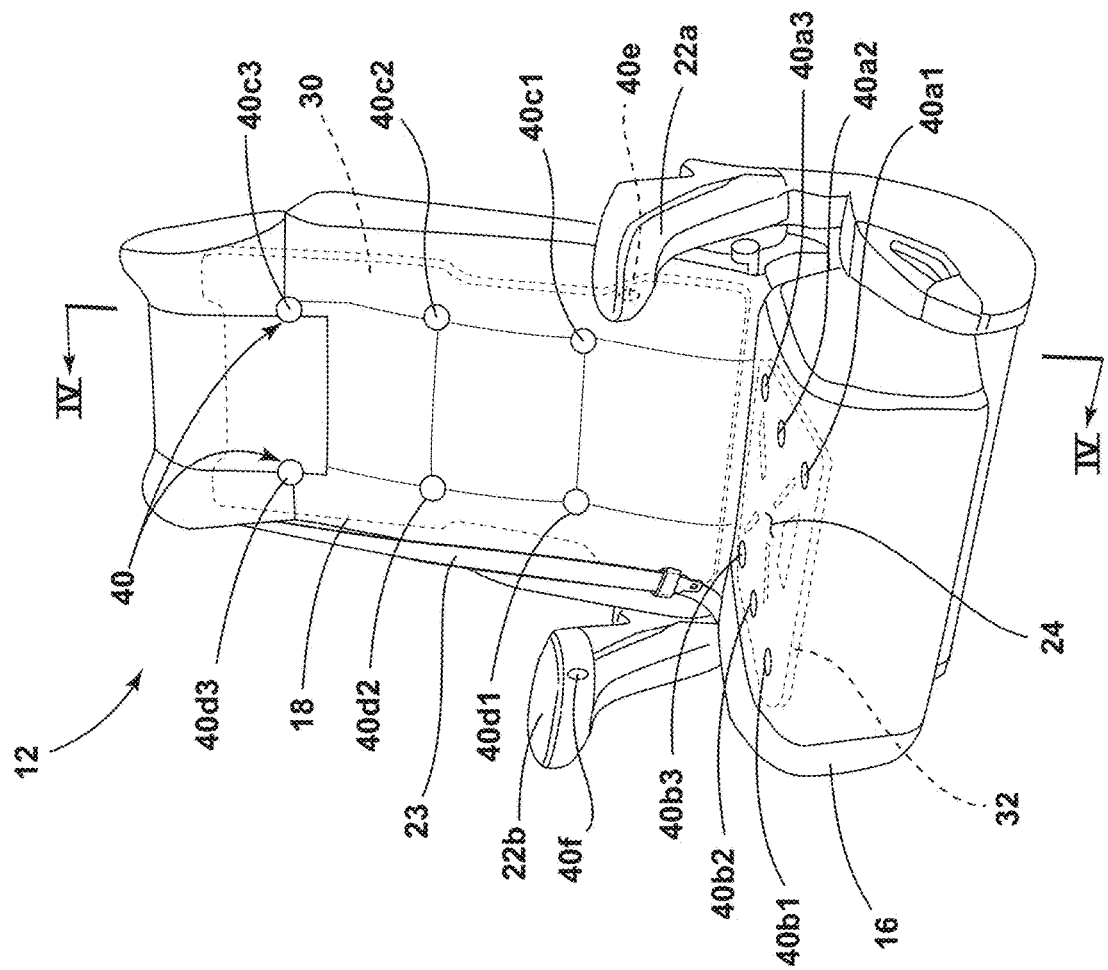
FIG. 3 is a front view of one of the seating assemblies of FIG. 2, illustrating the seating assembly having a seat, seatback, and armrests, with nozzles disposed at the seat, the seatback, and the armrests.
Figure 4:
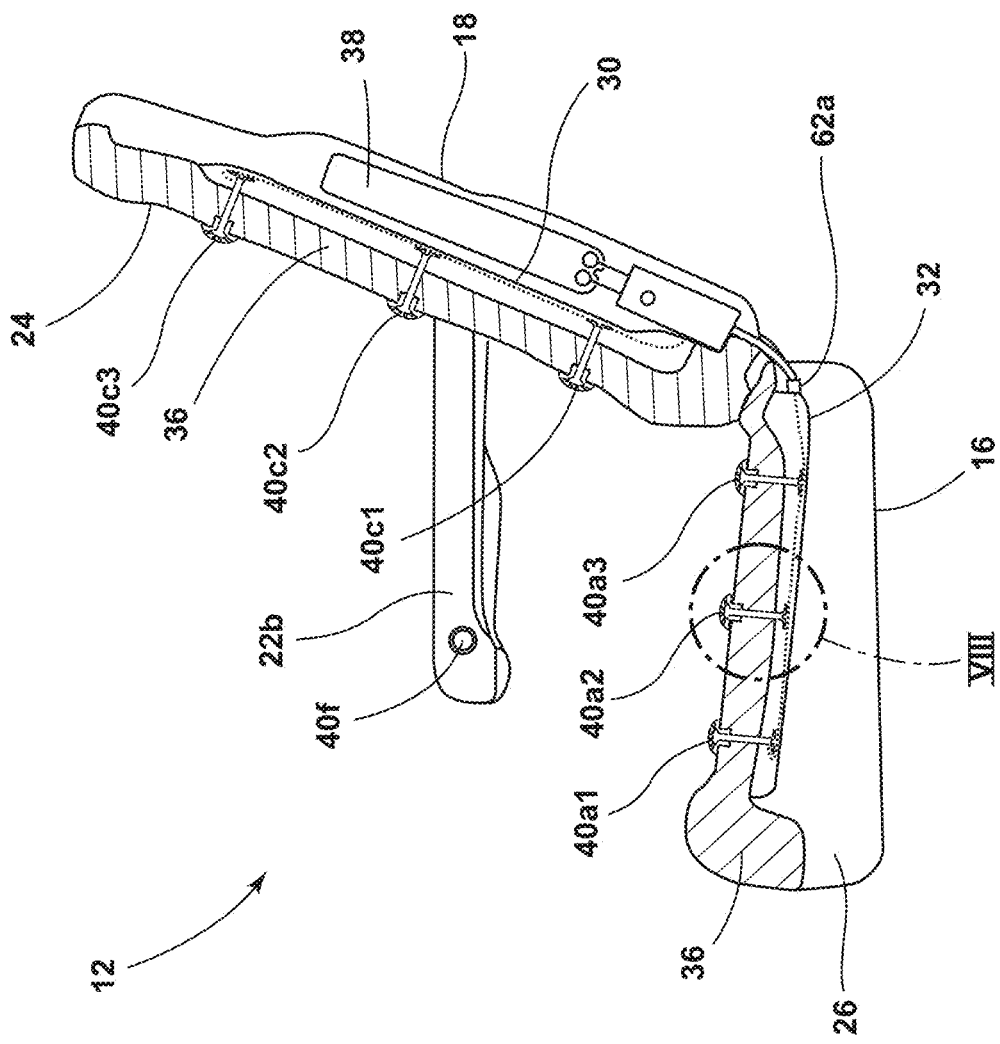
FIG. 4 is cross-sectional side view taken through the line IV-IV of FIG. 3, illustrating the seat having a first carrier within an interior of the seating assembly, the seatback having a second carrier within the interior of the seating assembly, a pressurized supply of liquid sanitizer within the interior of the seating assembly, and the nozzles extending into the interior of the seating assembly.

Referring now to FIGS. 3-4, each seating assembly 12 includes an exterior surface 24 and an interior 26 beneath the exterior surface 24. The exterior surface 24 includes the exterior surface 24 of the seating assembly 12 at the seat 16 and seatback 18 most likely to contact the person 20 when the person 20 occupies the seating assembly 12. A fabric 28 such as leather or vinyl can provide exterior surface 24. Alternatively, a rigid plastic can provide the exterior surface 24. These materials are not exclusive. The interior 26 can include a first carrier 30 at the seatback 18 and a second carrier 32 at the seat 16. The first carrier 30 and the second carrier 32 provide structural support within the interior 26. The first carrier 30 and the second carrier 32 together form a carrier system 34 for the seating assembly 12. The seating assembly 12 can include cushioning 36 disposed in the interior 26, including between the exterior surface 24 and the first carrier 30 and between the exterior surface 24 and the second carrier 32. The cushioning 36 provides comfort for the person 20 occupying the seating assembly 12.

Figure 5:
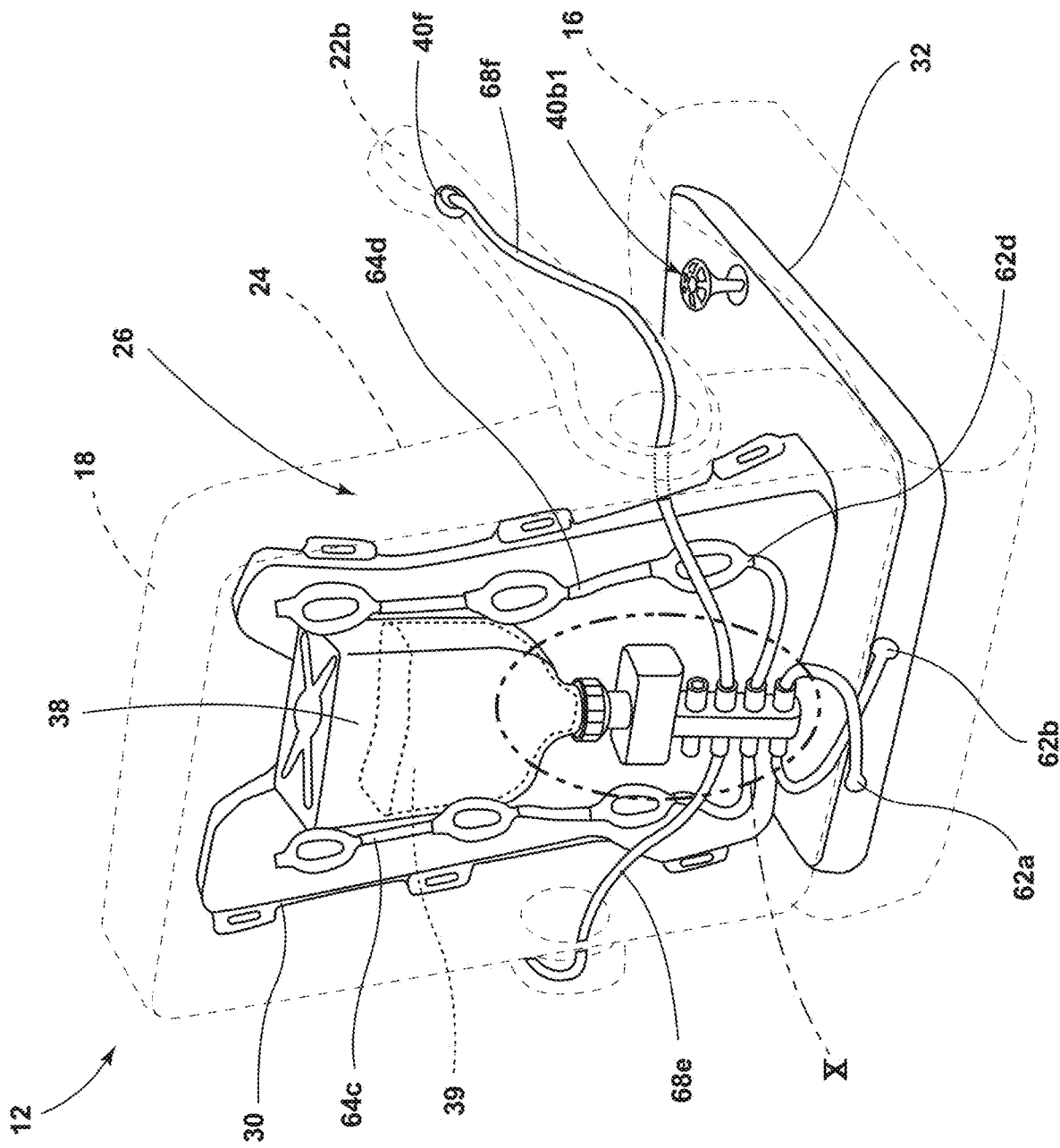
FIG. 5 is a rear perspective view of the seating assembly of FIG. 3, illustrating the exterior surface in phantom and the pressurized supply of liquid sanitizer disposed at the seatback.

Referring now additionally to FIG. 5, each seating assembly 12 includes a pressurized supply 38 of liquid sanitizer 39 disposed within the interior 26. The liquid sanitizer 39 can be any liquid that can be used to sanitize or disinfect the exterior surface 24 of the seating assembly 12. The liquid sanitizer 39 can include a substance, or mixture of substances, that reduces the bacteria population at the exterior surface 24 to which it is applied, as explained below, by significant numbers, but does not destroy or eliminate all bacteria. The liquid sanitizer 39 can include a substance, or mixture of substances, that destroys or irreversibly inactivates bacteria, fungi and viruses, but not necessarily bacterial spores, at the exterior surface 24 to which it is applied, as explained below. The active substance or substances in the liquid sanitizer 39 can include, without limitation, ethanol, dipropylene glycol, hypochlorites, chlorine dioxide, iodophores, peroxyacetic acid, quaternary ammonium compounds, benzylalkonium chloride, among others. The liquid sanitizer 39 can be aerosolized leaving the pressurized supply 38 to increase the ability of the liquid sanitizer 39 to reach the exterior surface 24 and a wider area thereof.

Figure 6:
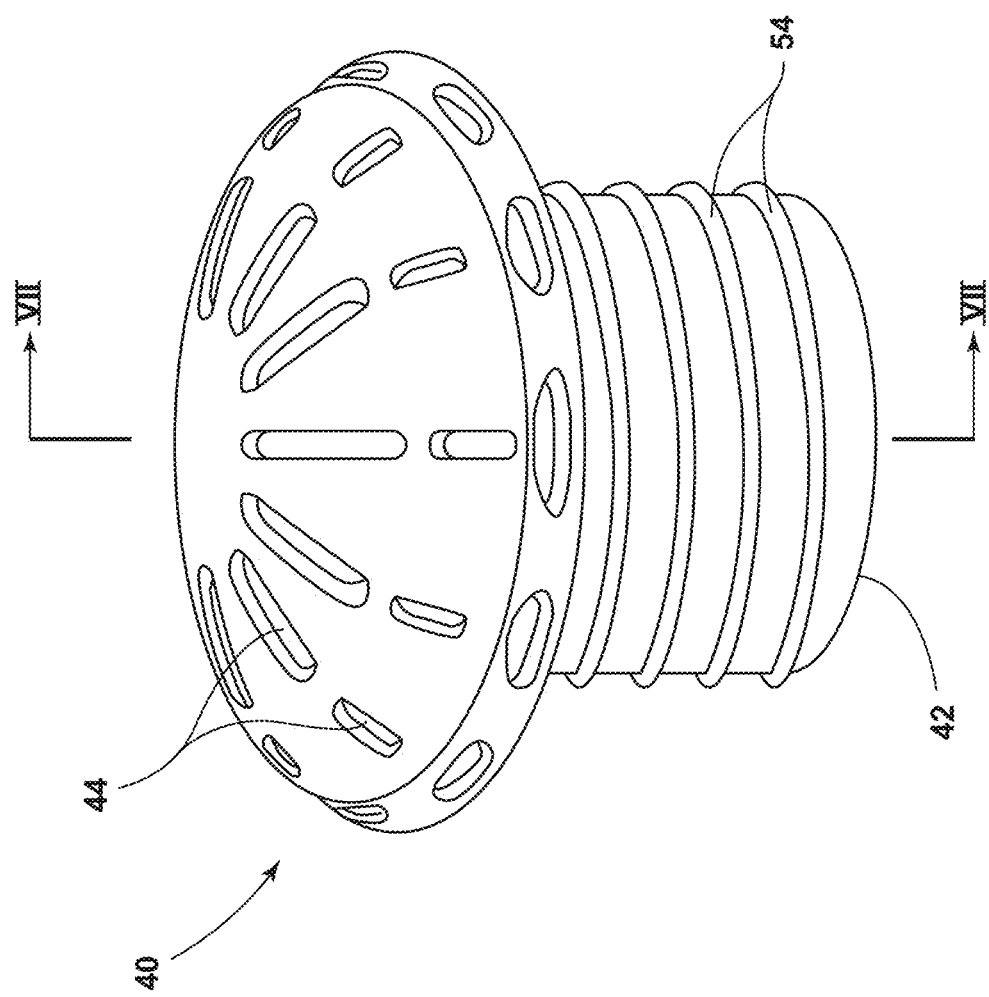
FIG. 6 is a perspective view of one of the plurality of nozzles incorporated into the seating assembly of FIG. 3, illustrating an inlet with outwardly extending threads and a plurality of perforations that are exposed over the exterior surface of the seating assembly.
Figure 7:
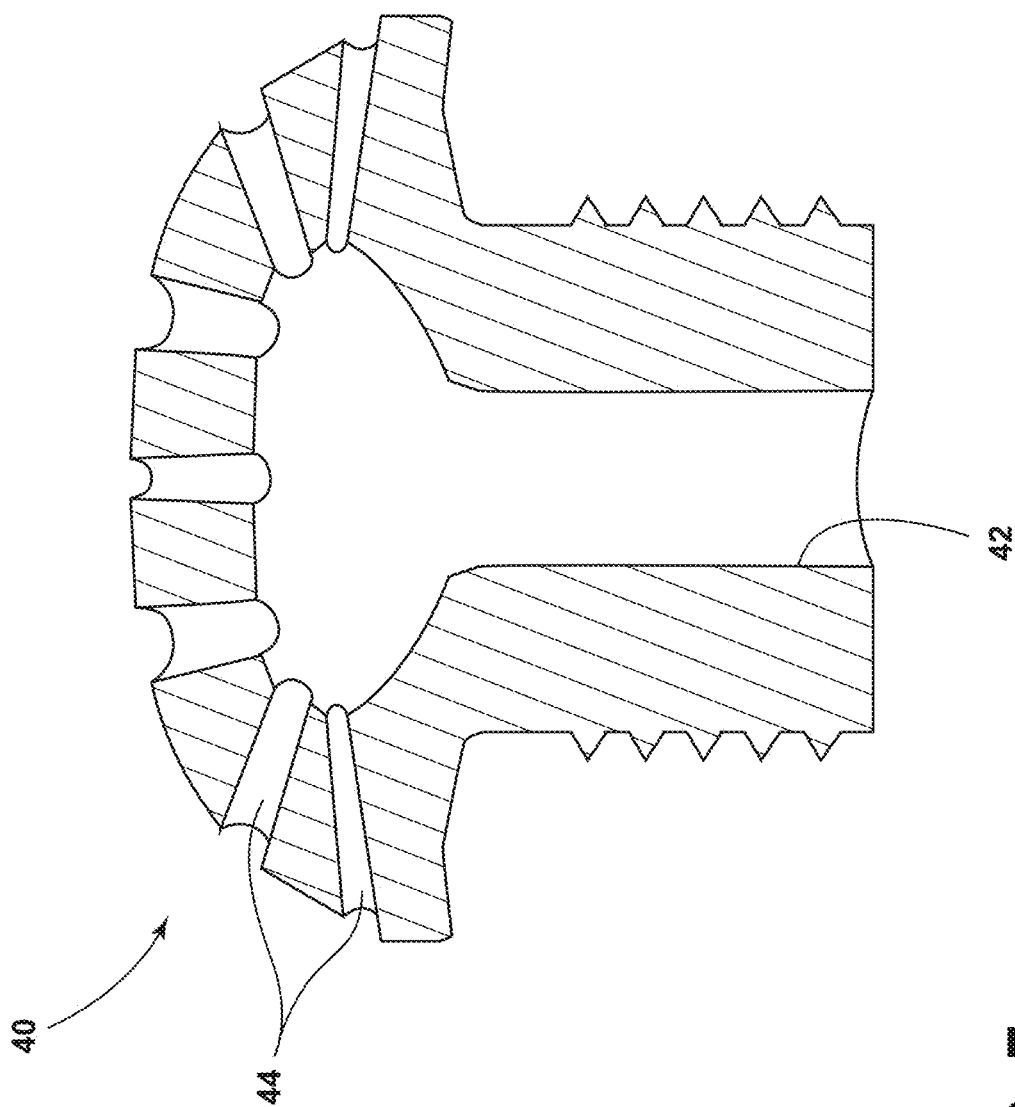
FIG. 7 is a cross-sectional side view of the nozzle of FIG. 6 taken through line VII-VII of FIG. 6, illustrating the inlet in fluid communication with the perforations.

Referring now additionally to FIGS. 6 and 7, each seating assembly 12 further includes one or more nozzles 40. In the illustrated embodiment, there are a plurality of nozzles 40. Because each of the nozzles 40 are the same, only one nozzle 40 will be described specifically. As explained further herein, the nozzles 40 are in fluid communication with the pressurized supply 38 of liquid sanitizer 39. The nozzle 40 directs the liquid sanitizer 39 onto the exterior surface 24, when the liquid sanitizer 39 is allowed to flow from the pressurized supply 38 of liquid sanitizer 39 to and through the nozzle 40. The nozzle 40 includes an inlet 42 and perforations 44 in fluid communication with the inlet 42. Liquid sanitizer 39 can flow into the nozzle 40 through the inlet 42 and then out of the nozzle 40 through the perforations 44. In some embodiments, like the illustrated embodiment, at least one of the plurality of nozzles 40 (40c1-40c3, 40d1-40d3) is positioned at the seatback 18 and directs the liquid sanitizer 39 onto the exterior surface 24 at the seatback 18, and at least one of the plurality of nozzles 40 (40a1-40a3, 40b1-40b3) is positioned at the seat 16 and directs the liquid sanitizer 39 on to the exterior surface 24 at the seat 16. Further, in some embodiments, like the illustrated embodiment, at least one of the plurality of nozzles 40 (40e, 40f) is positioned at one or both of the armrests 22a, 22b. In some embodiments, like the illustrated embodiment, the nozzle 40 functions and looks similar to an upholstery button, in that the nozzle 40 compresses a portion of the exterior surface 24 provided by the fabric 28 toward the interior 26, providing both a decorative and liquid directing/dispensing purpose. The nozzle 40 can be made from a rigid plastic providing the inlet 42, the inlet 42 being over-molded with a softer plastic providing the perforations 44 that are exposed to the person 20 over the exterior surface 24 of the seating assembly 12.

Figure 8:
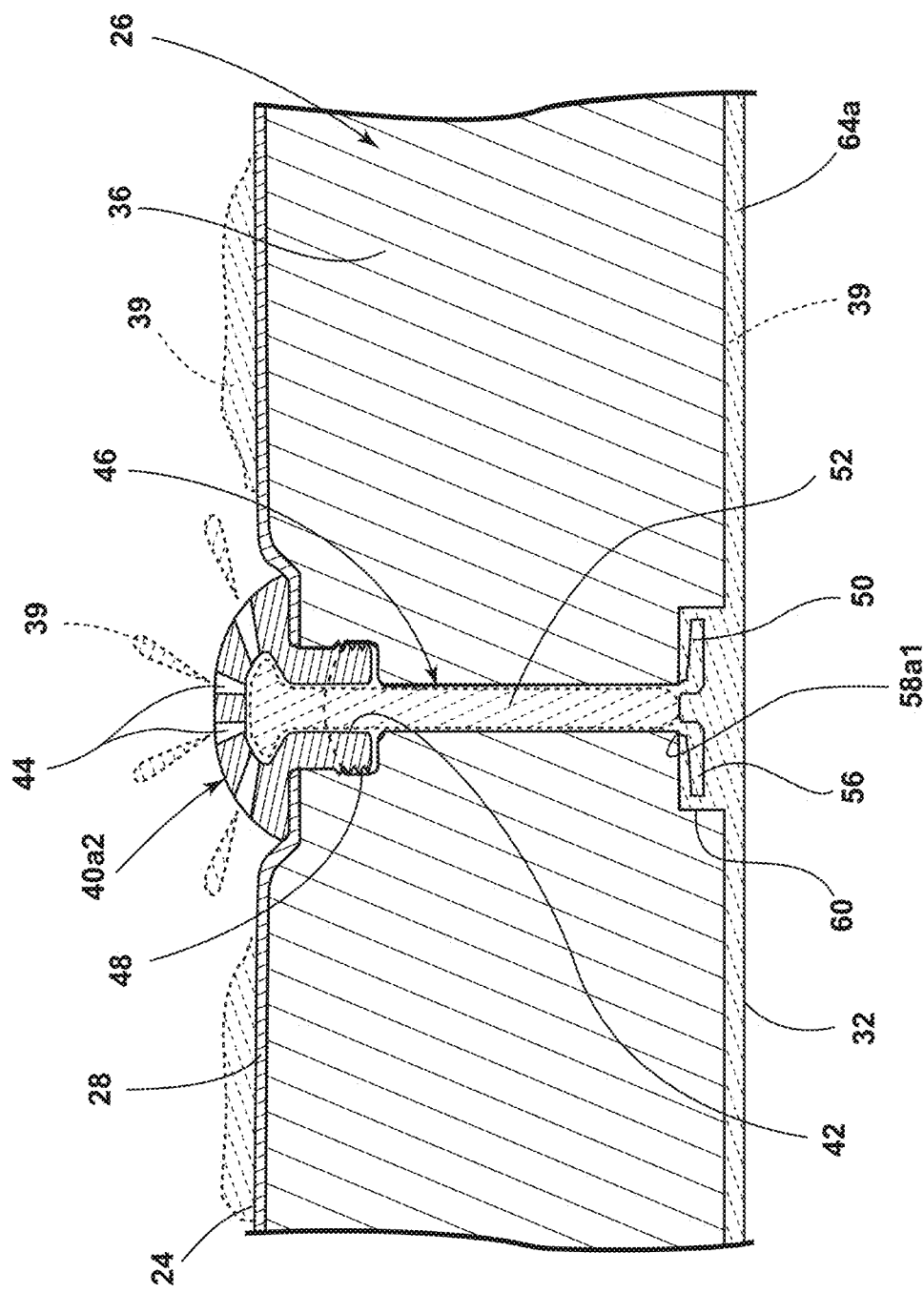
FIG. 8 is a close-up of area VIII of FIG. 4, illustrating the first carrier having a fluid communication pathway that is in fluid communication with a flexible conduit extending from the first carrier to one of the nozzles through cushioning disposed within the interior of the seat below the exterior surface, such that liquid sanitizer flows through the fluid communication pathway, through the flexible conduit, then out of the perforations of the nozzle onto the exterior surface.

Referring now to FIG. 8, one or more of the nozzles 40 is connected to a flexible conduit 46 that extends through the cushioning 36. The flexible conduit 46 includes a first end 48, a second end 50, and a tubular section 52 between the first end 48 and the second end 50. The first end 48 is attached to the inlet 42 of the nozzle 40. For example, as in the illustrated embodiment, the inlet 42 of the nozzle 40 can have threads 54 and the first end 48 of the flexible conduit 46 can have thread receivers (not illustrated) to receive the threads 54 of the nozzle 40. The first end 48 is attached to the inlet 42 of the nozzle 40 below the exterior surface 24, that is, within the interior 26. However, the perforations 44 remain exposed at the exterior surface 24 so that the nozzle 40 can direct (dispense) liquid sanitizer 39 to the exterior surface 24. There are many other ways that the nozzle 40 and flexible conduit 46 can become attached, such as through the use of a quarter-turn locking feature, friction over-fit, among other ways. The second end 50 of the flexible conduit 46 is attached to the first carrier 30 or second carrier 32, as the case may be, and is in fluid communication with the pressurized supply 38 of liquid sanitizer 39, as explained below. In the illustrated embodiment, the second end 50 of the flexible conduit 46 has a circular flange 56. The first carrier 30 and the second carrier 32 each in turn have an outlet 58 surrounding the tubular section 52 of any flexible conduit 46 extending therefrom and a flange receiver 60 that accepts and retains the circular flange 56 of any such flexible conduit 46. Each outlet 58 of the first carrier 30 and the second carrier 32, as the case may be, and the second end 50 of any flexible conduit 46 extending therefrom, are thus fluidly coupled.

Figure 9:
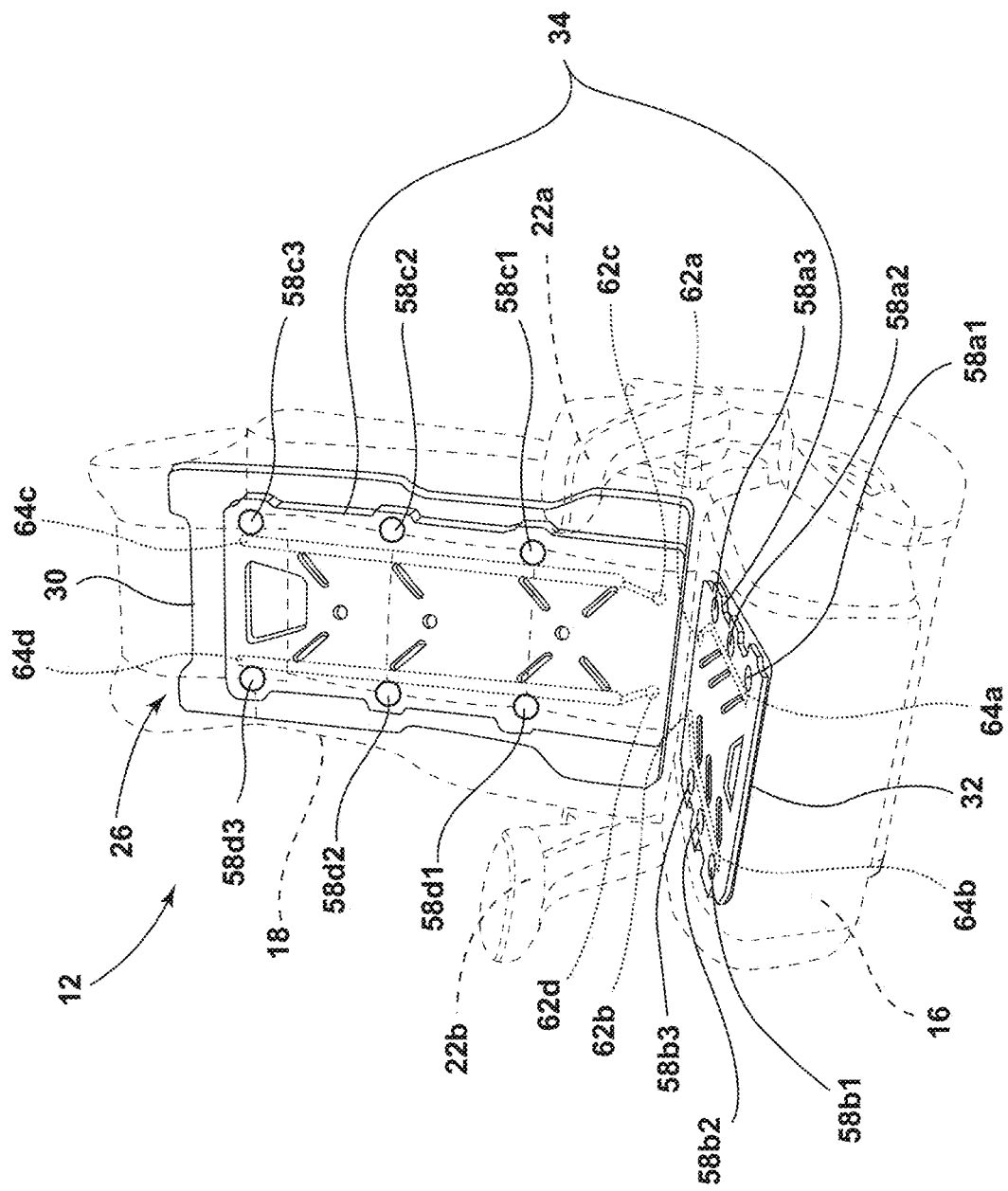
FIG. 9 is a perspective view into the interior of the seating assembly of FIG. 3, illustrating the first carrier at the seat and a second carrier at the seatback each having fluid communication pathways in fluid communication between inlets into the fluid communication pathways and outlets, each of which are in fluid communication with one of the plurality of nozzles.

Referring now additionally to FIG. 9, the outlet 58 is one of a plurality of outlets 58 provided by both the first carrier 30 and the second carrier 32. The first carrier 30 and the second carrier 32 provide an outlet 58 for each of the nozzles 40. Each outlet 58 is in fluid communication with one of the nozzles 40 via one of the flexible conduits 46 described above. Each of the first carrier 30 and the second carrier 32 include one or more inlets 62 for liquid sanitizer 39 to flow and fluid communication pathways 64 from each of the inlets 62 to one or more of the outlets 58. For example, in the illustrated embodiment, at the second carrier 32, the fluid communication passageway 64a leads from the inlet 62a to the outlets 58a1-58a3, and the fluid communication passageway 64b leads from the inlet 62b to the outlets 58b1-58b3. At the first carrier 30, the fluid communication passageway 64c leads from the inlet 62c to the outlets 58c1-58c3, and the fluid communication passageway 64d leads from the inlet 62d to the outlets 58d1-58d3. In the illustrated embodiment, the fluid communication passageways 64c, 64d and 64a, 64b are molded into the first carrier 30 and the second carrier 32, respectively.

Figure 10:
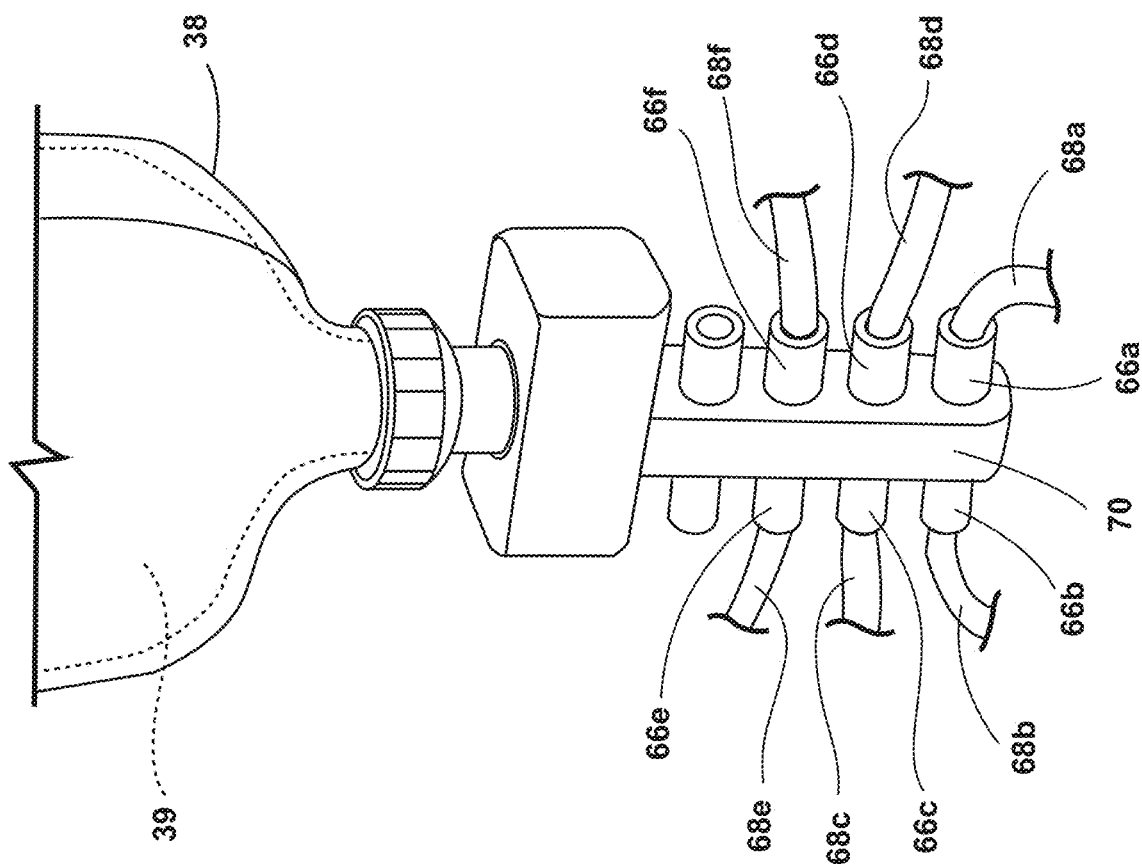
FIG. 10 is a close-up view of area X of FIG. 5, illustrating a plurality of valves in fluid communication with the pressurized supply of liquid sanitizer through a manifold, and tubing in fluid communication with each of the valves.

Referring now additionally to FIG. 10, the seating assembly 12 further includes one or more valves 66 in fluid communication between the pressurized supply 38 of liquid sanitizer 39 and the nozzles 40. In the illustrated embodiment, valve 66e is in fluid communication with the nozzle 40e disposed at the armrest 22a via tubing 68e. Valve 66f is in fluid communication with the nozzle 40f disposed at the other armrest 22b via tubing 68f. Valve 66a is in fluid communication with the nozzles 40a1-40a3 disposed at the second carrier 32 and in fluid communication with fluid communication pathway 68a, with tubing 64a providing the fluid communication between the valve 66a and the inlet 40b1-40b3 of the second carrier 32. Valve 66b is in fluid communication with the other nozzles 40 disposed at the first carrier 30 and in fluid communication with fluid communication pathway 64b, with tubing 68b providing the fluid communication between the valve 66b and the inlet 62b of the second carrier 32. Valve 66c is in fluid communication with the nozzles 40c1-40c3 disposed at the first carrier 30 and in fluid communication with fluid communication pathway 64c, with tubing 68c providing the fluid communication between the valve 66c and the inlet 62c of the first carrier 30. Valve 66d is in fluid communication with the other nozzles 40d1-40d3 disposed at the first carrier 30 and in fluid communication with fluid communication pathway 64d, with tubing 68d providing the fluid communication between the valve 66d and the other inlet 62d of the first carrier 30. Each of the valves 66a-66f are selectively positionable to and from (i) an open position where liquid sanitizer 39 from the pressurized supply 38 of liquid sanitizer 39 is able to flow and does flow through the valve 66a-66f to the one or more nozzles 40 serviced by the particular valve 66a-66f and (ii) a closed position where the liquid sanitizer 39 cannot flow through the valve 66a-66f to any nozzle 40. The valves 66a-66f are in fluid communication with the pressurized supply 38 of liquid sanitizer 39 through a manifold 70. The manifold 70 is in fluid communication with the pressurized supply 38 of liquid sanitizer 39 and the valves 66a-66f.

Figure 11:
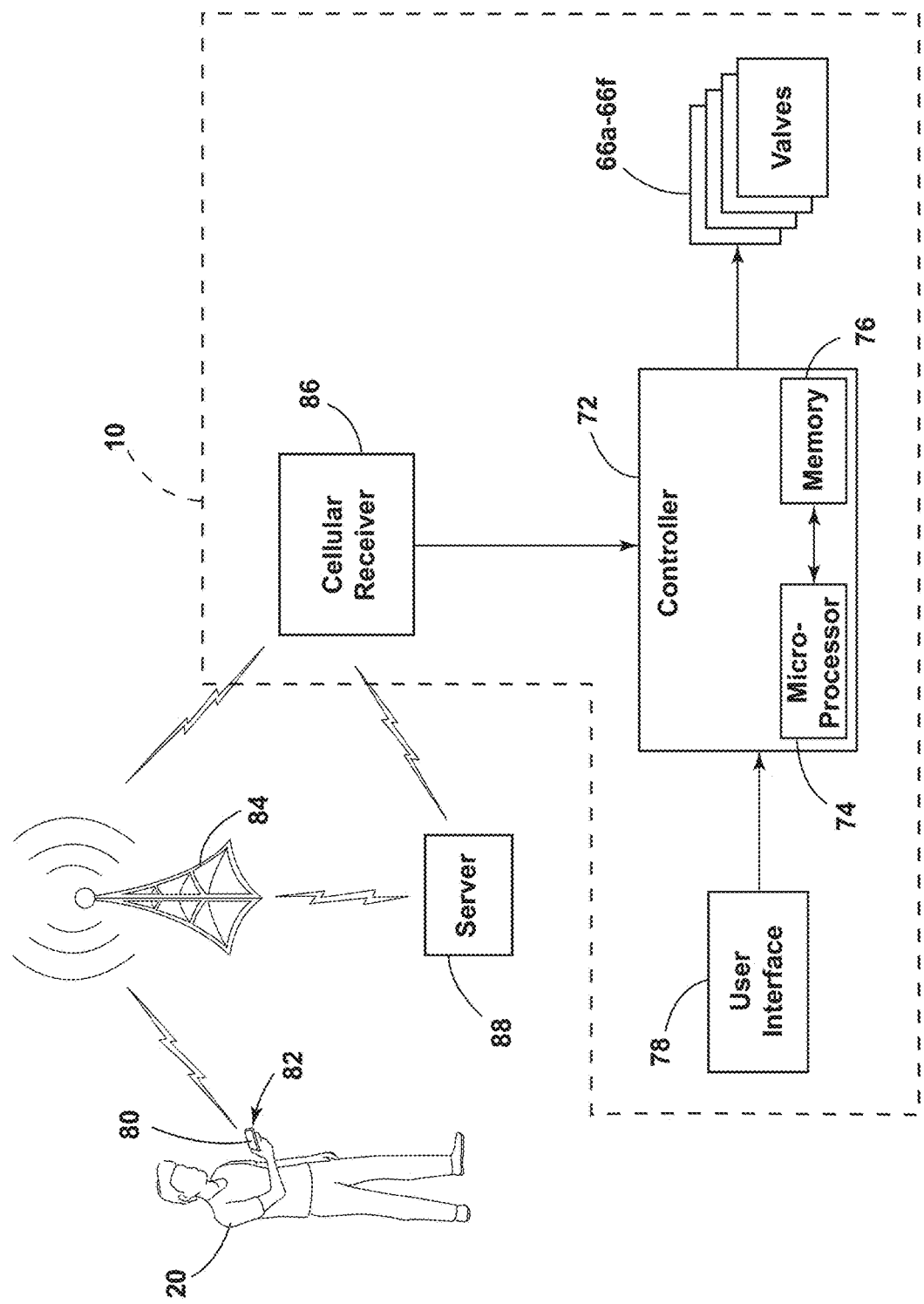
FIG. 11 is a schematic diagram of the vehicle of FIG. 1, illustrating a controller controlling operation of each of the plurality of valves in response to input from a user interface located within the vehicle or a user interface located at a mobile computing device outside of the vehicle being used by an anticipated passenger of the seating assembly of FIG. 3.

Referring now additionally to FIG. 11, the vehicle 10 includes a controller 72. The controller 72 includes a microprocessor 74 and memory 76. The microprocessor 74 executes programs that are stored in the memory 76 utilizing data stored in the memory 76 and provided to the controller 72 via various inputs. The controller 72 is communication with each of the valves 66a-66f and controls each of the valves 66a-66f to selectively cause any particular valve 66a-66f of the valves 66a-66f to move to and from the open position and the closed position. The controller 72 can cause one or more of the valves 66a-66f to move to the open position, in response to any one of a number of desired inputs, such as time of day (such as a nighttime self-cleaning session when nobody is aboard the vehicle 10), after reaching a destination and passengers have disembarked from the vehicle 10, and so on. Another input upon which the controller 72 can rely to control the valves 66a-66f is a user command (instruction) via a user interface 78. In such a case, the controller 72 is in communication with the user interface 78 and receives instructions from the user interface 78 regarding whether the controller 72 is to cause one or more or all of the valves 66a-66f to move to the open position. For example, the user interface 78 could be as simple as a "SANITIZE" button located at or near the seating assembly 12 at issue. Alternatively, the user interface 78 could be a touch screen display 80 located elsewhere within the interior 26, where the person 20 or operator (not illustrated) of the vehicle 10 cause the seating assembly 12 to become sanitized.

Alternatively or additionally, the user interface 78 can be disposed exterior of the vehicle 10. For example, in an embodiment, the user interface 78 is a touch screen display 80 on a mobile communications device 82 and the user command (instruction) inputted via the touch screen display 80 is transmitted to the controller 72. The person 20, before occupying the seating assembly 12, can use the touch screen display 80 as a user interface 78 to cause the controller 72 to sanitize the seating assembly 12 by causing the valves 66a-66f to open. The person 20 can do this as part of fee-based process to reserve the seating assembly 12 to transport the person 20 from one location to another location, such as for example, when the vehicle 10 is a bus used for intercity passenger transport. In addition to paying to reserve the seating assembly 12, the person 20 (as an anticipated passenger of the seating assembly 12 of the vehicle 10) can pay extra money to have the seat 16 sanitized or disinfected before the person 20 boards the vehicle 10 or otherwise occupies the seating assembly 12. The controller 72 is in communication with the mobile communications device 82. The mobile communications device 82 transmits the user command obtained from the touch screen display 80 to the cellular network 84, which in turn transmits the user command to a cellular receiver 86 in communication with the controller 72. The cellular network 84 can instead transmit the user command to a server 88, which is turns transmit the user command to the cellular receiver 86. In any event, the controller 72 causes the valves 66a-66f to move to the open position thus allowing the exterior surface 24 to be sanitized (or disinfected) before the person 20 (as the anticipated passenger) boards the vehicle 10 and occupies the seating assembly 12.

Figure 12:
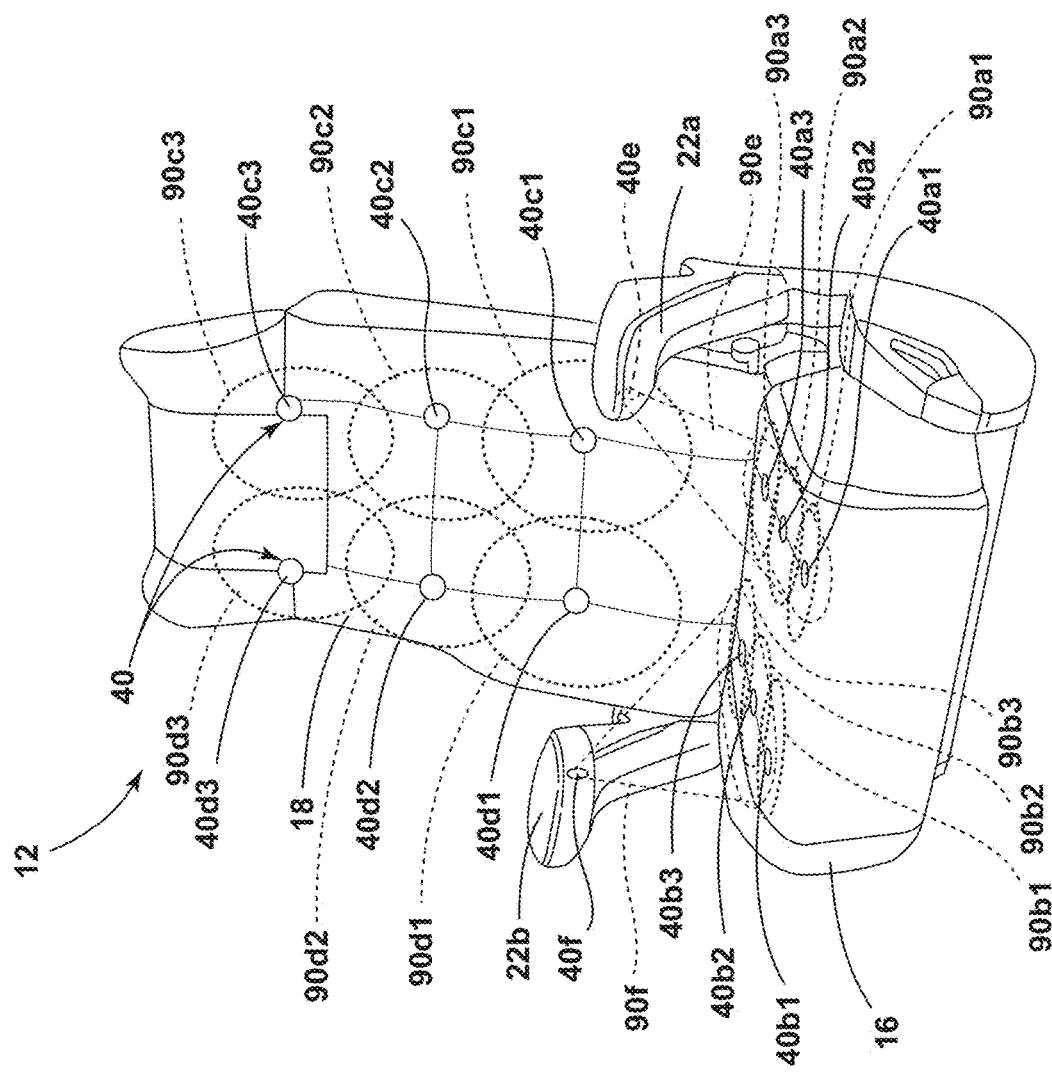
FIG. 12 is a front view of the seating assembly of FIG. 3, illustrating each of the plurality of nozzles directing liquid sanitizer onto a different but overlapping target area of the exterior surface of the seating assembly.

Referring now additionally to FIG. 12, each of the nozzles 40 are positioned to direct liquid sanitizer 39 onto a different target area 90 of the exterior surface 24. In the illustrated embodiment, each target area 90 overlaps with at least one other target area 90. When the controller 72 causes valve 66e to move from the closed position to the open position, liquid sanitizer 39 flows from the valve 66e toward the nozzle 40e. More specifically, when the controller 72 causes the valve 66e to be in the open position, liquid sanitizer 39 flows from the pressurized supply 38 of liquid sanitizer 39, through the manifold 70, through the valve 66e, through the tubing 68e, through the inlet 42 of the nozzle 40e, and out through the perforations 44 of the nozzle 40e, with the nozzle 40e directing the liquid sanitizer 39 onto the target area 90e of the exterior surface 24. When the controller 72 causes the valve 66e to move to the closed position, liquid sanitizer 39 cannot flow though the valve 66e to the nozzle 40e.

When the controller 72 causes valve 66f to move from the closed position to the open position, liquid sanitizer 39 flows from the valve 66f toward the nozzle 40f. More specifically, when the controller 72 causes the valve 66f to be in the open position, liquid sanitizer 39 flows from the pressurized supply 38 of liquid sanitizer 39, through the manifold 70, through the valve 66f, through the tubing 68f, through the inlet 42 of the nozzle 40f, and out through the perforations 44 of the nozzle 40f, with the nozzle 40f directing the liquid sanitizer 39 onto the target area 90f of the exterior surface 24. When the controller 72 causes the valve 66f to move to the closed position, liquid sanitizer 39 cannot flow though the valve 66f to the nozzle 40f.

When the controller 72 causes valve 66a to move from the closed position to the open position, liquid sanitizer 39 flows from the valve 66a toward the nozzles 40a1-40a3 of the second carrier 32. More specifically, when the controller 72 causes the valve 66a to be in the open position, liquid sanitizer 39 flows from the pressurized supply 38 of liquid sanitizer 39, through the manifold 70, through the valve 66a, through the tubing 68a, through the inlet 62a of the second carrier 32, through the fluid communication passageway 64a of the second carrier 32, through outlets 58a1-58a3, through flexible conduits 46, through the inlets 42 of the nozzles 40a1-40a3, and out through the perforations 44 of the nozzles 40a1-40a3, respectively, with the nozzles 40a1-40a3 directing the liquid sanitizer 39 onto the target areas 90a1-90a3 of the exterior surface 24, respectively. When the controller 72 causes the valve 66a to move to the closed position, liquid sanitizer 39 cannot flow though the valve 66a to the nozzles 40a1-40a3.

When the controller 72 causes valve 66b to move from the closed position to the open position, liquid sanitizer 39 flows from the valve 66b toward the nozzles 40b1-40b3 of the second carrier 32. More specifically, when the controller 72 causes the valve 66b to be in the open position, liquid sanitizer 39 flows from the pressurized supply 38 of liquid sanitizer 39, through the manifold 70, through the valve 66b, through the tubing 68b, through the inlet 62b of the second carrier 32, through the fluid communication passageway 64b of the second carrier 32, through outlets 58b1-58b3, through flexible conduits 46, through the inlets 42 of the nozzles 40b1-40b3, and out through the perforations 44 of the nozzles 40b1-40b3, respectively, with the nozzles 40b1-40b3 directing the liquid sanitizer 39 onto the target areas 90b1-90b3 of the exterior surface 24, respectively. When the controller 72 causes the valve 66b to move to the closed position, liquid sanitizer 39 cannot flow though the valve 66b to the nozzles 40b1-40b3.

When the controller 72 causes valve 66c to move from the closed position to the open position, liquid sanitizer 39 flows from the valve 66c toward the nozzles 40c1-40c3 of the first carrier 30. More specifically, when the controller 72 causes the valve 66c to be in the open position, liquid sanitizer 39 flows from the pressurized supply 38 of liquid sanitizer 39, through the manifold 70, through the valve 66c, through the tubing 68c, through the inlet 62c of the first carrier 30, through the fluid communication passageway 64c of the first carrier 30, through outlets 58c1-58c3, through flexible conduits 46, through the inlets 42 of the nozzles 40c1-40c3, and out through the perforations 44 of the nozzles 40c1-40c3, respectively, with the nozzles 40c1-40c3 directing the liquid sanitizer 39 onto the target areas 90c1-90c3 of the exterior surface 24, respectively. When the controller 72 causes the valve 66c to move to the closed position, liquid sanitizer 39 cannot flow though the valve 66c to the nozzles 40c1-40c3.

When the controller 72 causes valve 66d to move from the closed position to the open position, liquid sanitizer 39 flows from the valve 66d toward the nozzles 40d1-40d3 of the first carrier 30. More specifically, when the controller 72 causes the valve 66d to be in the open position, liquid sanitizer 39 flows from the pressurized supply 38 of liquid sanitizer 39, through the manifold 70, through the valve 66d, through the tubing 68d, through the inlet 62d of the first carrier 30, through the fluid communication passageway 64d of the first carrier 30, through outlets 58d1-58d3, through flexible conduits 46, through the inlets 42 of the nozzles 40d1-40d3, and out through the perforations 44 of the nozzles 40d1-40d3, respectively, with the nozzles 40d1-40d3 directing the liquid sanitizer 39 onto the target areas 90d1-90d3 of the exterior surface 24, respectively. When the controller 72 causes the valve 66d to move to the closed position, liquid sanitizer 39 cannot flow though the valve 66d to the nozzles 40d1-40d3.

Assuming that the seatbelt 23 is positioned to overlap one or more of the target areas 90, one or more of the nozzles 40 further directs liquid sanitizer 39 onto the seatbelt 23. The liquid sanitizer 39 sanitizer sanitizes and/or disinfects at least a portion of the seatbelt 23. In some embodiments, one or more nozzles 90 are disposed in a position dedicated to direct liquid sanitizer 39 onto the seatbelt 23.

Figure 13:
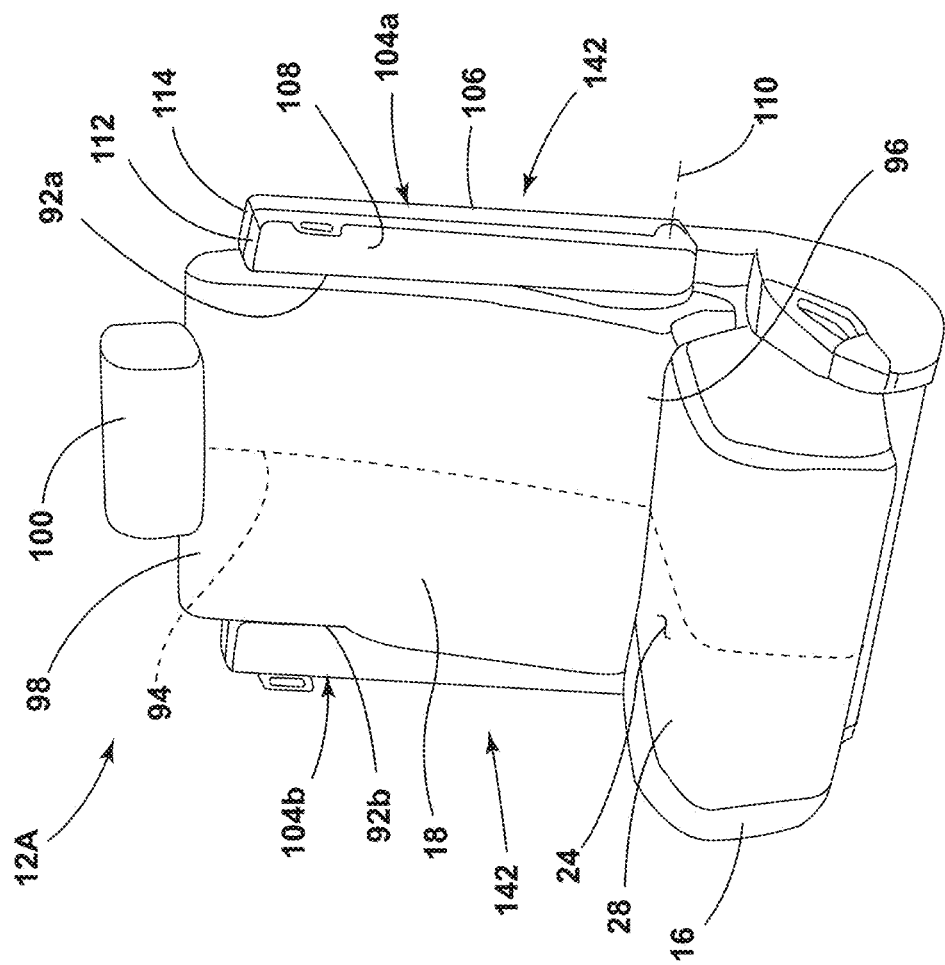
FIG. 13 is a perspective view of another seating assembly that can be used in the vehicle of FIG. 1, illustrating a first dispenser and a second dispenser of liquid sanitizer, each in a stowed position and disposed at lateral sides of the seatback.
Figure 14:
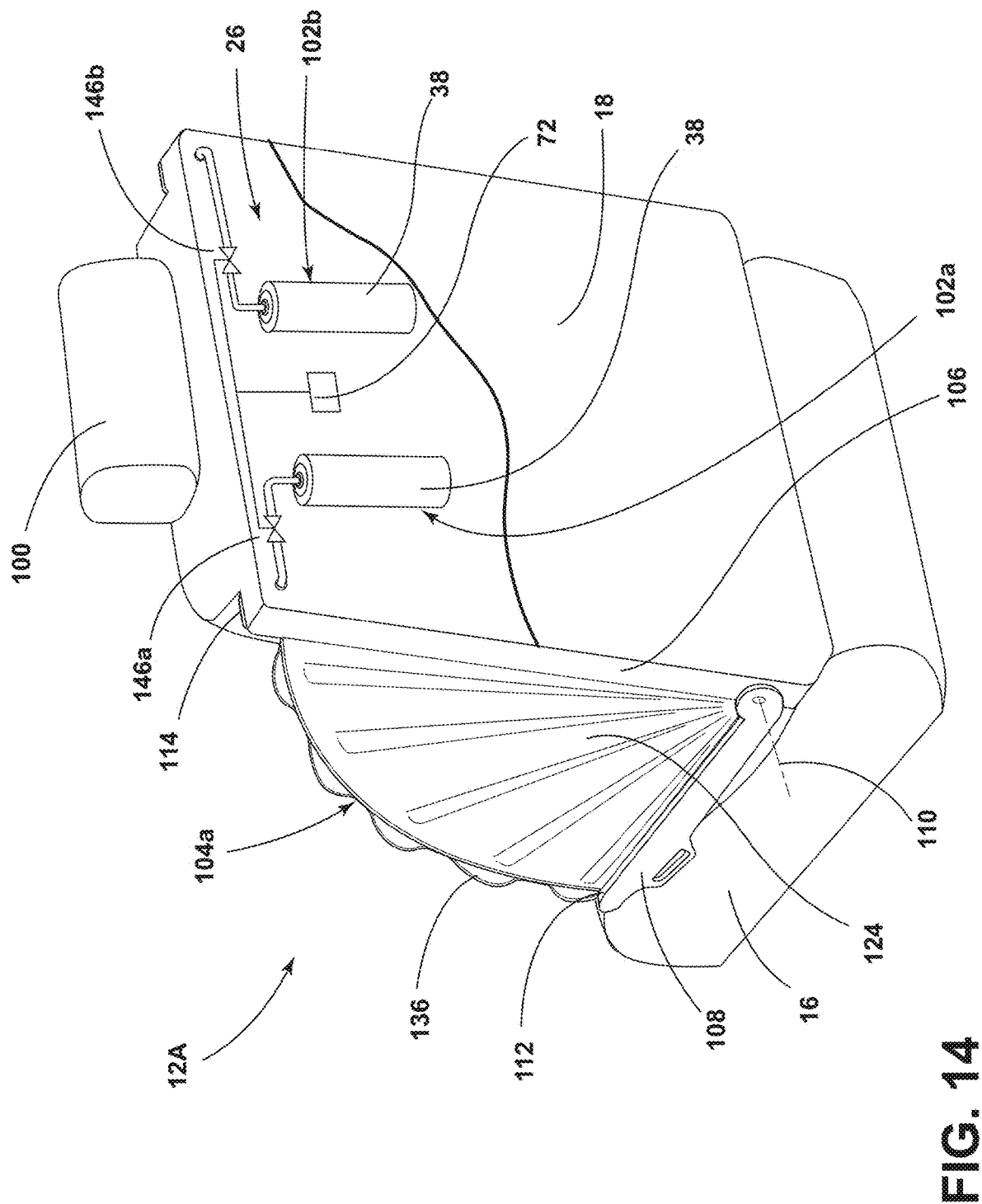
FIG. 14 is a rear perspective view of the seating assembly of FIG. 13, illustrating the first dispenser in a deployed position and the pressurized supply of liquid sanitizer disposed within the interior of the seating assembly at the seatback and in fluid communication with the first dispenser and the second dispenser through valves controlled by the controller.
Figure 15:
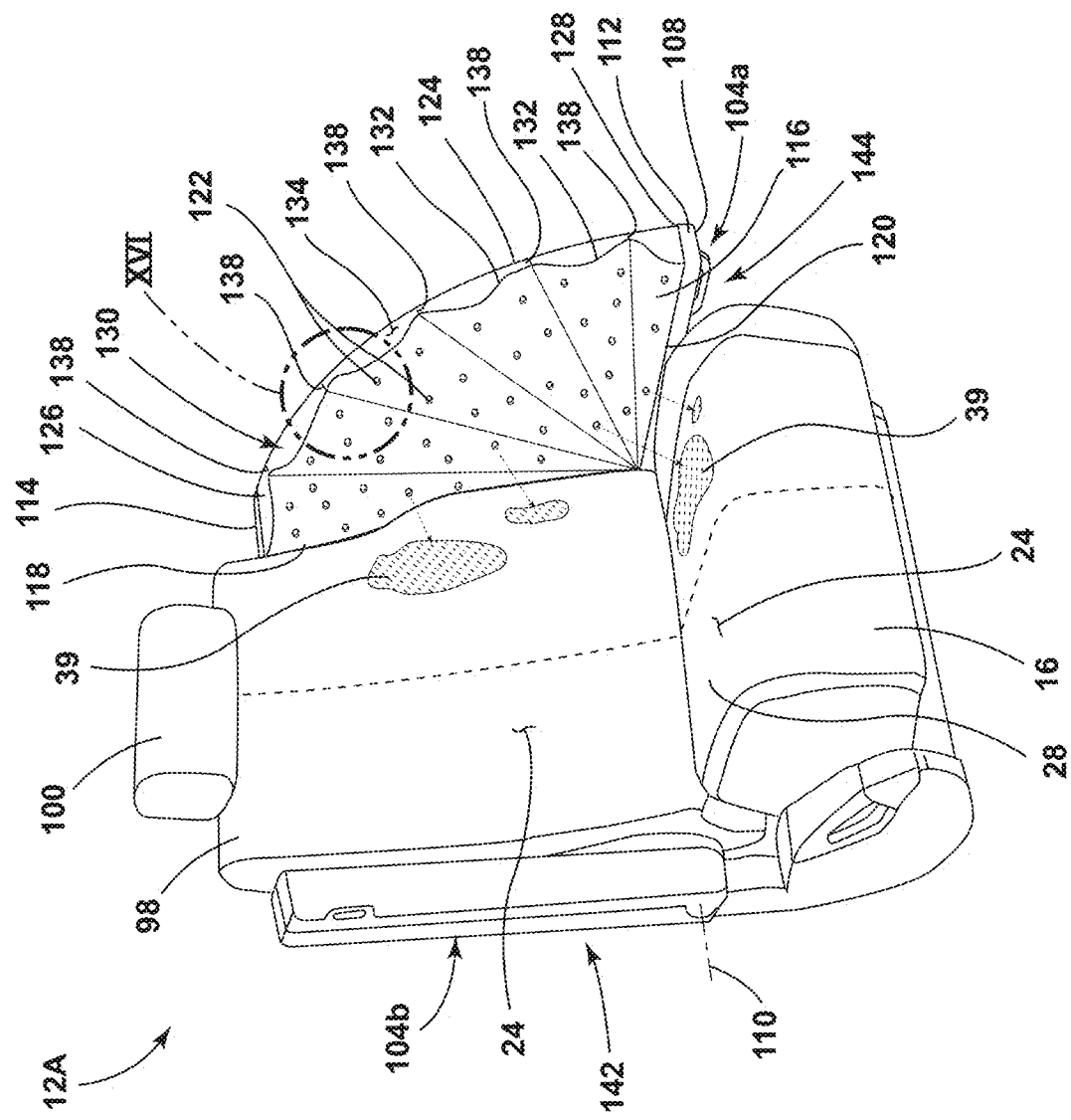
FIG. 15 is a front perspective view of the seating assembly of FIG. 13, illustrating the first dispenser in a deployed position where a first flexible sheet of material and a second flexible sheet of material are fanned out forming a fluid flow zone where the liquid sanitizer flows before exiting through perforations through the first flexible sheet of material and onto the exterior surface.
Figure 16:
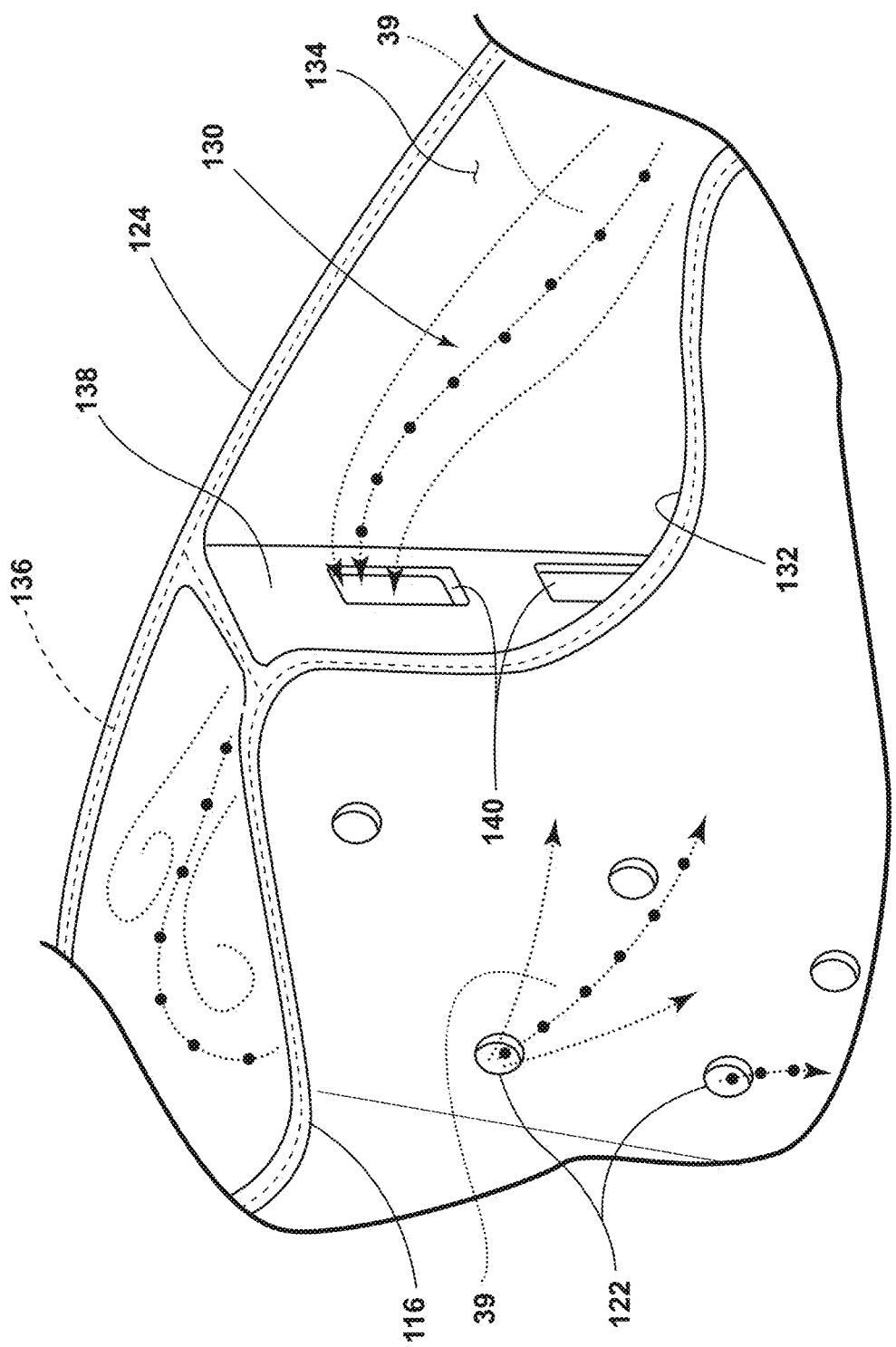
FIG. 16 is a close up view of area XVI of FIG. 15, illustrating dividers separating the first flexible sheet of material and the second flexible sheet of material, each divider having channels to allow the flow of liquid sanitizer through the dividers and to the perforations.

Referring now to FIGS. 13-15, another embodiment seating assembly 12A again includes a seat 16 and a seatback 18 cooperating with the seat 16 to support the person 20. The seating assembly 12 further includes an exterior surface 24, such as that provided by the fabric 28, and an interior 26 beneath the exterior surface 24. The seatback 18 has lateral sides 92a, 92b (relative to a midline 94), a bottom portion 96, and a top portion 98. The bottom portion 96 is disposed closer to the seat 16 than the top portion 98. The top portion 98 is disposed closer to a head restraint 100, if separately incorporated, than the bottom portion 96. Like the seating assembly 12, the seating assembly 12A includes a pressurized supply 38 of liquid sanitizer 39 disposed within the interior 26. In the illustrated embodiment, the pressurized supply 38 of liquid sanitizer 39 is two canisters 102a, 102b of the same, both of which are disposed in the interior 26 at the seatback 18.

The seating assembly 12 further includes a first dispenser 104a and a second dispenser 104b to direct liquid sanitizer 39 onto the exterior surface 24. The first dispenser 104a is disposed at one lateral side 92a, and the second dispenser 104b is disposed at the other lateral side 92b. The first dispenser 104a is a mirror image and otherwise identical to the second dispenser 104b. Therefore, only the first dispenser 104a will be particularly described. The first dispenser 104a includes a fixed base 106. The fixed base 106 extends along the lateral side 92a between the bottom portion 96 and the top portion 98 of the seatback 18. The fixed base 106 is fixed to the lateral side 92a of the seatback 18. The first dispenser 104a further includes a forward arm 108. The forward arm 108 is forward of the fixed base 106. The forward arm 108 is pivotally attached to the fixed base 106 and is so attached closer to the bottom portion 96 of the seatback 18 than to the top portion 98 of the seatback 18. The forward arm 108 pivots about an axis 110. The forward arm 108 has a furthest point 112 away from the axis 110. The fixed base 106 has a furthest point 114 away from the axis 110.

The first dispenser 104a further includes a first flexible sheet of material 116. The first flexible sheet of material 116 has a first end 118 and a second end 120. The first end 118 of the first flexible sheet of material 116 is attached to the fixed base 106. The second end 120 of the first flexible sheet of material 116 is attached to the forward arm 108. The first flexible sheet of material 116 has perforations 122 that are in fluid communication with the pressurized supply 38 of liquid sanitizer 39.

The first dispenser 104a further includes a second flexible sheet of material 124. The second flexible sheet of material 124 is layered next to the first flexible sheet of material 116, with the second flexible sheet of material 124 positioned laterally further away from the midline 94 of the seating assembly 12A than the first flexible sheet of material 116. Like the first flexible sheet of material 116, the second flexible sheet of material 124 is attached to the fixed base 106 at a first end 126 and attached to the forward arm 108 at a second end 128. The first flexible sheet of material 116 and the second flexible sheet of material 124 cooperate to form a fluid flow zone 130 between the two flexible sheets of material 116, 124. Both the first flexible sheet of material 116 and the second flexible sheet of material 124 have an interior surface 132, 134, respectively, that faces the fluid flow zone 130. A cover 136 connects the first flexible sheet of material 116 and the second flexible sheet of material 124 to cover and enclose the fluid flow zone 130.

A plurality of dividers 138 maintain separation between the first flexible sheet of material 116 and the second flexible sheet of material 124. Each divider 138 is attached to the interior surface 132 of the first flexible sheet of material 116 as well as the interior surface 134 of the second flexible sheet of material 124. Each divider 138 includes one or more channels 140 in fluid communication with the fluid flow zone 130. The one or more channels 140 allow for the flow of liquid sanitizer 39 through the plurality of dividers 138 to reach and exit through the perforations 122.

Each of the first dispenser 104a and the second dispenser 104b can take a stowed position 142 (see FIG. 13). In the stowed position 142, the forward arm 108 is adjacent to the fixed base 106. More specifically, in the stowed position 142, the furthest point 112 of the forward arm 108 is in closest proximity to the furthest point 114 of the fixed base 106. The first flexible sheet of material 116 and the second flexible sheet of material 124 are folded up together. In the stowed position 142, the first dispenser 104a and the second dispenser 104b are not dispensing liquid sanitizer 39 through the perforations 122 onto the exterior surface 24. In an embodiment, in the stowed position 142, the forward arm 108 and the fixed base 106 are flush together and form a housing to hide the first flexible sheet of material 116 and the second flexible sheet of material 124.

Each of the first dispenser 104a and the second dispenser 104b can take a deployed position 144, and can move to, from, and between the stowed position 142 and the deployed position 144. In FIGS. 14 and 15, the first dispenser 104a is illustrated in the deployed position 144, while the second dispenser 104b remains in the stowed position 142. It should be understood that the second dispenser 104b looks and performs in a mirror image manner to the first dispenser 104a, while the second dispenser 104b is also in the deployed position 144. In the deployed position 144, the forward arm 108 has rotated forward away from the fixed base 106, relative to the stowed position 142. In the deployed position 144, the first flexible sheet of material 116 and the second flexible sheet of material 124 are fanned out, and the first dispenser 104a (and the second dispenser 104b) are able to dispense liquid sanitizer 39 through the perforations 122 onto the exterior surface 24. The liquid sanitizer 39, when allowed to flow from the pressurized supply 38 of liquid sanitizer 39, flows from the pressurized supply 38 of liquid sanitizer 39 and through the fluid flow zone 130 before exiting through the perforations 122 through the first flexible sheet of material 116.

The seating assembly 12 further includes at least one valve 146a in fluid communication with and between the pressurized supply 38 of liquid sanitizer 39 and the first dispenser 104a, and at least one valve 146b in fluid communication with and between the pressurized supply 38 of liquid sanitizer 39 and the second dispenser 104b. In the illustrated embodiment, because the pressurized supply 38 of liquid sanitizer 39 is split into two canisters 102a, 102b—one for each of the first dispenser 104a and the second dispenser 104b—there are two valves 146a, 146b—one in fluid communication with and between each of the canisters 102a, 102b and the first dispenser 104a and the second dispenser 104b, respectively. Each of the valves 146a, 146b are selectively positionable to and from an open position. In the open position, liquid sanitizer 39 flows through the valve 146a to the first dispenser 104a, and liquid sanitizer 39 flows through the valve 146b to the second dispenser 104b. In the closed position, liquid sanitizer 39 cannot flow through the valve 146a to the first dispenser 104a, and liquid sanitizer 39 cannot flow through the valve 146b to the second dispenser 104b.

The controller 72 is in communication with each of the valves 146a, 146b, to cause one or both valves 146a, 146b to move to and from the open position and the closed position. The controller 72 causes the valve 146a to move to the open position only when the first dispenser 104a is in the deployed position 144. The controller 72 causes the valve 146b to move to the open position only when the second dispenser 104b is in the deployed position 144. As with the previous seating assembly 12, the controller 72 is configured to receive instructions from the user interface 78 regarding whether the controller 72 is to cause the valves 146a, 146b to move to the open position. When the valves 146a, 146b are in the open position and the first dispenser 104a and the second dispenser 104b are in the deployed position 144, liquid sanitizer 39 flows from the pressurized supply 38 of liquid sanitizer 39, through the perforations 122 of the first dispenser 104a and the second dispenser 104b and onto the exterior surface 24. The exterior surface 24 thus becomes sanitized and in some embodiments disinfected. The first dispenser 104a faces the second dispenser 104b, in the deployed position 144. The first dispenser 104a and the second dispenser 104b dispense liquid sanitizer 39 onto the exterior surface 24 from generally opposite directions thus creating overlapping areas of coverage of liquid sanitizer 39 onto the exterior surface 24.

The seating assemblies 12, 12A described herein provide visual confirmation that the exterior surface 24 has been sanitized or disinfected. The person 20, as the anticipated passenger of the seating assemblies 12, 12A, thus feels more comfortable occupying the seating assembly 12, 12A.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the afore-mentioned structure without departure from the concepts of the present disclosure, and further it is to be understood that such concepts are intended to be covered by the following claims unless these claims by their language expressly state otherwise.

What is claimed is:

1. A seating assembly for a vehicle comprising:
   an exterior surface;
   an interior beneath the exterior surface;
   a seat;
   a seatback cooperating with the seat, the seatback having lateral sides, a bottom portion, and a top portion;
   a pressurized supply of liquid sanitizer disposed within the interior; and
   a dispenser disposed at one of the lateral sides of the seatback, the dispenser including:
     a fixed base that extends along the lateral side from between the bottom portion of the seatback and the top portion of the seatback;
     a forward arm pivotally attached to the fixed base closer to the bottom portion of the seatback than the top portion of the seatback;
     a first flexible sheet of material attached at one end to the fixed base and at another end to the forward arm, the first flexible sheet of material having perforations in fluid communication with the pressurized supply of liquid sanitizer;
     a stowed position where the forward arm is adjacent to the fixed base with the first flexible sheet of material folded together and the dispenser not dispensing liquid sanitizer through the perforations onto the exterior surface; and
     a deployed position where the forward arm is rotated forward away from the fixed base with the first flexible sheet of material fanned out and the dispenser dispenses liquid sanitizer through the perforations onto the exterior surface.

2. The seating assembly of claim 1 further comprising:
   a second flexible sheet of material layered next to the first flexible sheet of material, with the second flexible sheet of material being positioned laterally further away from a midline of the seating assembly than the first flexible sheet of material, the second flexible sheet of material and the first flexible sheet of material cooperating to form a fluid flow zone between the second flexible sheet of material and the first flexible sheet of material, with the first flexible sheet of material and the second flexible sheet of material having an interior surface facing the fluid flow zone;
   in the stowed position, the second flexible sheet of material and the first flexible sheet of material are folded together; and in the deployed position, the second flexible sheet of material is also fanned out, and liquid sanitizer flows within the fluid flow zone between the first flexible sheet of material and the second flexible sheet of material before exiting through the perforations of the first flexible sheet of material.

3. The seating assembly of claim 2 further comprising:
a plurality of dividers, each attached to the interior surface of the first flexible sheet of material and the second flexible sheet of material, maintaining separation between the first flexible sheet of material and the second flexible sheet of material, and including channels in fluid communication with the fluid flow zone to allow for the flow of liquid sanitizer through the plurality of dividers.

4. The seating assembly of claim 1 further comprising:
a valve in fluid communication with and between the pressurized supply of liquid sanitizer and the dispenser, the valve selectively positionable to and from an open position where the liquid sanitizer flows through the valve to the dispenser and a closed position where the liquid sanitizer cannot flow through the valve to the dispenser; and
a controller in communication with the valve to cause the valve to move to, from, and between the open position and the closed position, the controller configured to receive instructions from a user interface regarding whether the controller is to cause the valve to move to the open position.

5. The seating assembly of claim 1 further comprising:
a second dispenser disposed at the other of the lateral sides of the seatback, the second dispenser including:
  a fixed base that extends along the lateral side from between the bottom portion of the seatback and the top portion of the seatback;
  a forward arm pivotally attached to the fixed base closer to the bottom portion of the seatback than the top portion of the seatback;
  a first flexible sheet of material attached at one side to the fixed base and at another side to the forward arm, the first flexible sheet of material having perforations in fluid communication with the pressurized supply of liquid sanitizer;
  a stowed position where the forward arm is adjacent to the fixed base with the first flexible sheet of material folded together and the dispenser not dispensing liquid sanitizer through the perforations onto the exterior surface;
  a deployed position where the forward arm is rotated forward away from the fixed base with the first flexible sheet of material fanned out and the dispenser dispenses liquid sanitizer through the perforations onto the exterior surface; and
  when the dispenser is in the deployed position and the second dispenser is in the deployed position, the dispenser faces the second dispenser, and the dispenser and the second dispenser dispense liquid sanitizer onto the exterior surface from generally opposite directions.

6. A vehicle comprising:
a seating assembly with an exterior surface, a dispenser, and a source of liquid sanitizer in liquid communication with the dispenser, the source and the dispenser collectively being configured to dispense the liquid sanitizer out of the dispenser and onto the exterior surface;
wherein, (i) the seating assembly further comprises a seat and a seatback having lateral sides, and (ii) the dispenser is disposed at one of the lateral sides of the seatback;
wherein, the dispenser comprises (i) a fixed base that extends along the lateral side, between a bottom portion and a top portion of the seatback, and (ii) a forward arm forward of the fixed base that is pivotally attached to the fixed base;
wherein, the dispenser further comprises (i) a first flexible sheet of material, the first flexible sheet of material comprising a first end attached to the fixed base and a second end attached to the forward arm, and (ii) perforations through the first flexible sheet of material; and
the liquid sanitizer flows through the perforations to dispense the liquid sanitizer.

7. The vehicle of claim 6 further comprising:
a second dispenser disposed at the other of the lateral sides of the seatback, the second dispenser in liquid communication with the source of the liquid sanitizer, and the second dispenser and the source are collectively configured to dispense the liquid sanitizer out of the dispenser and onto the exterior surface.

8. The vehicle of claim 6, wherein
the dispenser further comprises (i) a second flexible sheet of material layered next to the first flexible sheet of material, the second flexible sheet of material comprising a first end attached to the fixed base and a second end attached to the forward arm;
the first flexible sheet of material and the second sheet of material cooperate to form a fluid flow zone between the first flexible sheet of material and the second sheet of material; and
the liquid sanitizer flows through the fluid flow zone before flowing through the perforations.

9. The vehicle of claim 6, wherein
the dispenser comprises a deployed position and a stowed position that is different than the deployed position; and
the dispenser dispenses the liquid sanitizer while in the deployed position but not the stowed position.

10. The vehicle of claim 9, wherein
the liquid sanitizer flows through the perforations while the dispenser is in the deployed position.

11. The vehicle of claim 10, wherein
the first flexible sheet of material fans out when the dispenser moves from the stowed position to the deployed position.

12. The vehicle of claim 11, wherein
the dispenser further comprises (i) a second sheet of material that also fans out when the dispenser moves from the stowed position to the deployed position, and (ii) a fluid flow zone between the first sheet of material and the second sheet of material, and the liquid sanitizer flows through the fluid flow zone before exiting through the perforations through the first flexible sheet of material.

13. The vehicle of claim 6, wherein
the seating assembly further comprises an interior; and
the source of the liquid sanitizer is disposed within the interior.

14. The vehicle of claim 6, wherein
the source of the liquid sanitizer is pressurized.

15. The vehicle of claim 6, wherein
the seating assembly further comprises (i) a valve in fluid communication between the dispenser and the source of the liquid sanitizer, and (ii) a controller in communication with the valve to selectively open or close the valve.

16. The vehicle of claim 15, wherein
the controller opens the valve upon receiving instructions from a user interface.

17. The vehicle of claim 16, wherein
the user interface is disposed exterior of the vehicle.

18. A vehicle comprising:
a seating assembly with an exterior surface, a dispenser, and a source of liquid sanitizer in liquid communication with the dispenser, the source and the dispenser collectively being configured to dispense the liquid sanitizer out of the dispenser and onto the exterior surface;
wherein, the dispenser comprises a flexible sheet of material with perforations, through which perforations the liquid sanitizer flows while the liquid sanitizer is dispensed onto the exterior surface.

19. The vehicle of claim 18, wherein
the seating assembly further comprises a seat and a seatback having lateral sides; and
the dispenser is disposed at one of the lateral sides of the seatback.

20. The vehicle of claim 18, wherein
the dispenser comprises a deployed position and a stowed position that is different than the deployed position;
the first flexible sheet of material fans out when the dispenser moves from the stowed position to the deployed position; and
the dispenser dispenses the liquid sanitizer while in the deployed position but not the stowed position.

* * * * *